US012297435B2

(12) United States Patent
Roberts et al.

(10) Patent No.: US 12,297,435 B2
(45) Date of Patent: May 13, 2025

(54) **MUTATIONS IN *Streptococcus pyogenes* Cas9 DISCOVERED BY BROAD SCANNING MUTAGENESIS DEMONSTRATE ENHANCEMENT OF DNA CLEAVAGE ACTIVITY**

(71) Applicant: INTEGRATED DNA TECHNOLOGIES, INC., Coralville, IA (US)

(72) Inventors: Nathaniel Hunter Roberts, Iowa City, IA (US); Liyang Zhang, North Liberty, IA (US); Christopher Anthony Vakulskas, North Liberty, IA (US)

(73) Assignee: Integrated DNA Technologies, Inc., Coralville, IA (US)

( * ) Notice: Subject to any disclaimer, the term of this patent is extended or adjusted under 35 U.S.C. 154(b) by 0 days.

(21) Appl. No.: 17/857,262

(22) Filed: Jul. 5, 2022

(65) Prior Publication Data
US 2023/0203505 A1 Jun. 29, 2023

Related U.S. Application Data

(60) Provisional application No. 63/217,881, filed on Jul. 2, 2021.

(51) Int. Cl.
*C12N 15/52* (2006.01)
*C12N 9/22* (2006.01)
*C12N 15/11* (2006.01)

(52) U.S. Cl.
CPC .............. *C12N 15/52* (2013.01); *C12N 9/22* (2013.01); *C12N 15/111* (2013.01); *C12N 2310/20* (2017.05)

(58) Field of Classification Search
None
See application file for complete search history.

(56) References Cited

U.S. PATENT DOCUMENTS

| | | | |
|---|---|---|---|
| 11,242,542 B2 * | 2/2022 | Vakulskas | C12N 9/22 |
| 2018/0100148 A1 * | 4/2018 | Vakulskas | C12N 15/11 |
| 2018/0320201 A1 | 11/2018 | Vakulskas et al. | |
| 2023/0133277 A1 * | 5/2023 | Vakulskas | C12N 15/902 435/462 |

OTHER PUBLICATIONS

Vakulskas, C.A. et al. "A high-fidelity Cas9 mutant delivered as a ribonucleoprotein complex enables efficient gene editing in human hematopoietic stem and progenitor cells." Nature Medicine. vol. 24. (Aug. 2018), pp. 1216-1224. (Year: 2018).*
Spencer, J.M. et al. "Deep mutational scanning of S. pyogenes Cas9 reveals important functional domains". Scientific Reports, vol. 7 (2017), p. 16836. (Year: 2017).*
Babu, K. et al. "Bridge Helix of Cas9 modulates target DNA cleavage and mismatch tolerance". Biochemistry, vol. 58 (2019), pp. 1905-1917. (Year: 2019).*
Bratovic, M. et al. "Bridge helix arginines play a critical role in Cas9 sensitivity to mismatches." Nature Chemical Biology, vol. 16 (May 2020), pp. 587-595. (Year: 2020).*
Spencer, J.M. et al. "Deep mutational scanning of S. pyogenes Cas9 reveals important functional domains". Scientific Reports, vol. 7 (2017), p. 16836.Supplemental Data sheet. (Year: 2017).*
International Search Report from International Searching Authority for PCT/US2022/036079 dated Feb. 2, 2023.
International Preliminary Report of Patentability for PCT/US2022/036079 dated Dec. 14, 2023.
Anzalone AV, Randolph PB, Davis JR, Sousa AA, Koblan LW, Levy JM, Chen PJ, Wilson C, Newby GA, Raguram A, Liu DR. Search-and-replace genome editing without double-strand breaks or donor DNA. Nature. Dec. 2019;576 (7785): 149-157. doi: 10.1038/s41586-019-1711-4. Epub Oct. 21, 2019. PMID: 31634902; PMCID: PMC6907074.
Walton RT, Christie KA, Whittaker MN, Kleinstiver BP. Unconstrained genome targeting with near-PAMless engineered CRISPR-Cas9 variants. Science. Apr. 17, 2020;368(6488):290-296. doi: 10.1126/science.aba8853. Epub Mar. 26, 2020. PMID: 32217751; PMCID: PMC7297043.
Vakulskas CA, Dever DP, Rettig GR, Turk R, Jacobi AM, Collingwood MA, Bode NM, McNeill MS, Yan S, Camarena J, Lee CM, Park SH, Wiebking V, Bak RO, Gomez-Ospina N, Pavel-Dinu M, Sun W, Bao G, Porteus MH, Behlke MA. A high-fidelity Cas9 mutant delivered as a ribonucleoprotein complex enables efficient gene editing in human hematopoietic stem and progenitor cells. Nat Med. Aug. 2018;24(8):1216-1224. doi: 10.1038/s41591-018-0137-0. Epub Aug. 6, 2018. PMID: 30082871; PMCID: PMC6107069.
Kim HK, Yu G, Park J, Min S, Lee S, Yoon S, Kim HH. Predicting the efficiency of prime editing guide RNAs in human cells. Nat Biotechnol. Feb. 2021;39(2): 198-206. doi: 10.1038/s41587-020-0677-y. Epub Sep. 21, 2020. Erratum in: Nat Biotechnol. Mar. 2024;42(3):529. doi: 10.1038/s41587-024-02159-6. PMID: 32958957.

(Continued)

*Primary Examiner* — Anna Skibinsky
*Assistant Examiner* — Alexandra Geraldine Dace Denito
(74) *Attorney, Agent, or Firm* — Potomac Law Group, PLLC; Reza Mollaaghababa; Joseph F. Murphy

(57) ABSTRACT

This invention pertains to mutant Cas9 nucleic acids and proteins for use in CRISPR/Cas endonuclease systems, and their methods of use. In particular, the invention pertains to an isolated mutant Cas9 protein, wherein the isolated mutant Cas9 protein is active in a CRISPR/Cas endonuclease system, wherein the CRISPR/Cas endonuclease system displays increased on-target editing activity relative to a wild-type CRISPR/Cas endonuclease system. The invention also includes isolated nucleic acids encoding mutant Cas9 proteins, ribonucleoprotein complexes and CRISPR/Cas endonuclease systems having mutant Cas9 proteins that display increased on-target editing activity relative to a wild-type CRISPR/Cas endonuclease system.

14 Claims, 5 Drawing Sheets
Specification includes a Sequence Listing.

(56) References Cited

OTHER PUBLICATIONS

Song M, Kim HK, Lee S, Kim Y, Seo SY, Park J, Choi JW, Jang H, Shin JH, Min S, Quan Z, Kim JH, Kang HC, Yoon S, Kim HH. Sequence-specific prediction of the efficiencies of adenine and cytosine base editors. Nat Biotechnol. Sep. 2020;38(9):1037-1043. doi: 10.1038/s41587-020-0573-5. Epub Jul. 6, 2020. PMID: 32632303.

* cited by examiner

SEQUENCE LISTING

```
Sequence total quantity: 6
SEQ ID NO: 1            moltype = AA   length = 1368
FEATURE                 Location/Qualifiers
REGION                  1..1368
                        note = SYNTHETIC
source                  1..1368
                        mol_type = protein
                        organism = synthetic construct
SEQUENCE: 1
MDKKYSIGLD IGTNSVGWAV ITDEYKVPSK KFKVLGNTDR HSIKKNLIGA LLFDSGETAE   60
ATRLKRTARR RYTRRKNRIC YLQEIFSNEM AKVDDSFFHR LEESFLVEED KKHERHPIFG  120
NIVDEVAYHE KYPTIYHLRK KLVDSTDKAD LRLIYLALAH MIKFRGHFLI EGDLNPDNSD  180
VDKLFIQLVQ TYNQLFEENP INASGVDAKA ILSARLSKSR RLENLIAQLP GEKKNGLFGN  240
LIALSLGLTP NFKSNFDLAE DAKLQLSKDT YDDDLDNLLA QIGDQYADLF LAAKNLSDAI  300
LLSDILRVNT EITKAPLSAS MIKRYDEHHQ DLTLLKALVR QQLPEKYKEI FFDQSKNGYA  360
GYIDGGASQE EFYKFIKPIL EKMDGTEELL VKLNREDLLR KQRTFDNGSI PHQIHLGELH  420
AILRRQEDFY PFLKDNREKI EKILTFRIPY YVGPLARGNS RFAWMTRKSE ETITPWNFEE  480
VVDKGASAQS FIERMTNFDK NLPNEKVLPK HSLLYEYFTV YNELTKVKYV TEGMRKPAFL  540
SGEQKKAIVD LLFKTNRKVT VKQLKEDYFK KIECFDSVEI SGVEDRFNAS LGTYHDLLKI  600
IKDKDFLDNE ENEDILEDIV LTLTLFEDRE MIEERLKTYA HLFDDKVMKQ LKRRRYTGWG  660
RLSRKLINGI RDKQSGKTIL DFLKSDGFAN RNFMQLIHDD SLTFKEDIQK AQVSGQGDSL  720
HEHIANLAGS PAIKKGILQT VKVVDELVKV MGRHKPENIV IEMARENQTT QKGQKNSRER  780
MKRIEEGIKE LGSQILKEHP VENTQLQNEK LYLYYLQNGR DMYVDQELDI NRLSDYDVDH  840
IVPQSFLKDD SIDNKVLTRS DKNRGKSDNV PSEEVVKKMK NYWRQLLNAK LITQRKFDNL  900
TKAERGGLSE LDKAGFIKRQ LVETRQITKH VAQILDSRMN TKYDENDKLI REVKVITLKS  960
KLVSDFRKDF QFYKVREINN YHHAHDAYLN AVVGTALIKK YPKLESEFVY GDYKVYDVRK 1020
MIAKSEQEIG KATAKYFFYS NIMNFFKTEI TLANGEIRKR PLIETNGETG EIVWDKGRDF 1080
ATVRKVLSMP QVNIVKKTEV QTGGFSKESI LPKRNSDKLI ARKKDWDPKK YGGFDSPTVA 1140
YSVLVVAKVE KGKSKKLKSV KELLGITIME RSSFEKNPID FLEAKGYKEV KKDLIIKLPK 1200
YSLFELENGR KRMLASAGEL QKGNELALPS KYVNFLYLAS HYEKLKGSPE DNEQKQLFVE 1260
QHKHYLDEII EQISEFSKRV ILADANLDKV LSAYNKHRDK PIREQAENII HLFTLTNLGA 1320
PAAFKYFDTT IDRKRYTSTK EVLDATLIHQ SITGLYETRI DLSQLGGD            1368

SEQ ID NO: 2            moltype = DNA  length = 4251
FEATURE                 Location/Qualifiers
misc_feature            1..4251
                        note = SYNTHETIC
source                  1..4251
                        mol_type = other DNA
                        organism = synthetic construct
SEQUENCE: 2
atgggcagca gcgccccaaa gaagaagcgg aaggtcggta tccacggagt cccagcagcc   60
atggacaaaa agtactctat tggcctggat atcgggacca cagcgtcgg gtgggctgtt  120
atcaccgacg agtataaagt accttcgaaa aagttcaaag tgctgggcaa caccgatcgc  180
cattcaatca aaaagaactt gattggtgcg ctgttgtttg actccgggga aaccgccgag  240
gcgactcgcc ttaaacgtac agcacgtcgc cggtacactc ggcgtaagaa tcgcatttgc  300
tatttgcagg aaatctttag caacgagatg gcaaaagtcg atgactgtt tttccaccgc  360
ctcgaggaaa gctttctggt ggaggaagac aaaaagcatg agcgtcaccc gatcttcggc  420
aacattgtcg atgaagtagc gtatcatgaa aaatacccaa ccatttacca cttacgcaaa  480
aagctggtgg acagcactga caaagctgat ttgcgcctta tctatttagc cctggcacat  540
atgattaagt ttcgtggtca cttcctgatc gaaggagact taaatcccga caacagtgat  600
gttgataaat tgtttattca gcttgtccaa acttacaatc aactgttcga ggaaaacccg  660
```

```
atcaatgcct ccggtgtgga tgcaaaagcc attttaagtg cacgccttag caagtcccgt  720
cgcttagaaa accttatcgc gcagctgccc ggcgagaaaa agaatggttt gtttgggaac  780
cttattgcct tgagcttagg cctcaccccg aatttcaaaa gtaatttcga tcttgcagaa  840
gacgccaaat tacaactgtc gaaggatact tatgatgacg atctcgataa tctgttagcg  900
cagattggtg accaatacgc cgatcttttt ctggcggcta aaaatctgag cgacgccatc  960
ttgctttcgg atattctccg cgttaacacc gaaatcacga aagcgcctct tagtccagc  1020
atgattaaac gttatgatga acaccaccag gacctgacct tactcaaagc gttggttcgc  1080
cagcaactgc cagagaagta caaagaaatc ttctttgatc agtcaaagaa tggttatgcc  1140
ggctatattg acggggtgc aagccaagag gaattctaca aatttatcaa gcctattctg  1200
gagaaaatgg atggcaccga agagttattg gtgaagctta accgtgaaga cctcctgcgg  1260
aaacagcgca cattcgataa tggttcgatc ccacaccaaa tccatttggg ggagttacac  1320
gctattttgc gtcgcagga agactttac cctttcctga aggataaccg ggagaaaatt  1380
gagaagatcc ttacctttcg tattccgtat tacgtaggcc ccttagcacg gggtaatagc  1440
cgtttcgcgt ggatgacacg gaagtcgaa gagcgatca cccgtggaa cttcgaagag  1500
gtagtcgaca agggcgcatc agcgcagtct tttattgaac gtatgacgaa tttcgataaa  1560
aacttgccca atgagaaggt gcttccgaaa cattccttgt tatatgaata ttttacagtt  1620
tacaacgagc tgaccaaggt taaatacgtg acggaaggaa tgcgcaagcc cgcttttctt  1680
agcggtcagc aaaaaaaggc gatcgtcgac ctgttattca aaacgaatcg taaggtgact  1740
gtaaagcaac tcaaagaaga ttacttcaaa aagattgagt gcttcgacag cgtcgaaatc  1800
tctggggtag aggatcggtt taacgcaagt ttaggtacct accatgacct gcttaaaatc  1860
attaaggata aagacttctt agataatgaa gagaacgaag atattctcga ggacatcgtc  1920
ttgacgttaa cctatttga ggatcgtgaa atgattgaag aacgcctcaa aacttatgcc  1980
cacctgttcg acgataaggt gatgaagcag ctgaaacgtc ggcgctacac aggatggggc  2040
cgcttgagtc gcaaacttat taacggaatc cgtgacaagc aatccggcaa aacgattctg  2100
gatttcttga agtcggacgg atttgctaat cgcaacttca tgcagttgat ccatgatgac  2160
tccctgactt ttaaaggaa tattcaaaag gcgcaggtta gtggtcaagg cgacagctta  2220
cacgaacaca tcgcaaattt ggctggttcg ccggccatta aaaagggat cctccagaca  2280
gtgaaagttg tagatgagct tgttaaggtc atgggtcgtc ataagcccga aaacatcgtg  2340
attgaaatgg cgcgggagaa tcaaacgacc cagaaaggac aaaagaatag ccgtgaacgg  2400
atgaagcgga tcgaggaagg cattaaagag ctggggtctc aaatcttgga ggaacaccct  2460
gtggagaaca ctcagctcca aaatgaaaaa ctttacctgt actatttgca gaacggacgc  2520
gatatgtacg tggaccaaga gttggatatt aatcggctga gtgactacga cgttgatcat  2580
atcgtcccgc agagcttcct caaagacgat tctattgaca ataaggtact gacgcgctct  2640
gataaaaacc gtggtaagtc ggacaacgtg ccctccgaag aggttgtgaa aaagatgaaa  2700
aattattgcg gccagctttt aaacgcgaag ctgatcacac aacgtaaatt cgataatttg  2760
accaaggctg aacggggtgg cctgagcgag ttagataagg caggatttat taaacgccag  2820
ttagtgagaa ctcgtcaaat caccaaaacat gtcgcgcaga ttttgacag ccggatgaac  2880
accaagtacg atgaaaatga caaactgatc cgtgaggtga agtcattac tctgaagtcc  2940
aaattagtta gtgatttccg gaaggacttt caattccaca agtccgtga aattaataac  3000
tatcatcacg cacatgacgc gtacctgaat gcagtggttg ggaccgcct tatcaagaaa  3060
tatcctaagc tggagtcgga gttgtctat ggcgactata aggtatacga tgttcgcaaa  3120
atgattgcga aatctgagca ggagatcggt aaggcaaccg caaatatttt cttttactca  3180
aacattatga atttctttaa gacagaaatc actctggcca acggggagat tcgcaaacgt  3240
ccgttgatcg aaacaaacgg cgagactggc gaaattgttt gggacaaagg cgtgatttc  3300
gcgacggtgc gcaaggtact gagcatgcct caagtcaata ttgttaagaa aaccgaagtg  3360
cagacgggcg ggttttccaa ggaaagcatc ttacccaaac gtaattcaga taaacttatt  3420
gcacgcaaaa aggactggga tccgaaaaag tatggagct tcgacagtcc aaccgtagcc  3480
tactctgttc tcgttgtagc gaaagtagaa aagggtaaat ccaagaaact gaaatctgtc  3540
aaggagttgc ttggaatcac cattatggag cgtagctcct tcgagaagaa cccgattgac  3600
tttctggaag ccaaaggata taagaggtc aagaagatc ttatcattaa gctgcctaag  3660
tattcactct tcgagctgga aaatggtcgt aaacgcttgc tgcttctgc cggcgagttg  3720
cagaagggca atgaattagc acttccatca aagtacgtta acttcctgta tttggccagc  3780
cattacgaga aactgaaggg gtccagag gacaacgaac agaaacaatt atttgtagag  3840
cagcacaagc attatcttga tgaaatcatt gagcaaattt ccgaattcag taaacgcgta  3900
atcctggccg atgcaaacct cgacaaggtg ctgagcgctt acaataagca tcgcgacaaa  3960
cctatccgtg agcaggctga aaatatcatt cacctgttca cattaacgaa cctgggcgct  4020
ccggccgctt ttaaatattt cgacacgaca atcgaccgta agcgctatac cagtacgaaa  4080
gaagtgttgg atgcgaccct tattcaccag tcaattacag gattatatga gacccgtatc  4140
gaccttagcc aattaggtgg ggatgcggcc ccgaagaaaa aacgcaaagt ggatccgaag  4200
aaaaaacgca agtggcggc cgcactcgag caccaccacc accaccactg a             4251
```

```
SEQ ID NO: 3             moltype = DNA   length = 4290
FEATURE                  Location/Qualifiers
misc_feature             1..4290
                         note = SYNTHETIC
source                   1..4290
                         mol_type = other DNA
                         organism = synthetic construct
SEQUENCE: 3
atgggcaagc ccatccctaa ccccctgttg gggctggaca gcaccgctcc caaaagaaa    60
aggaaggtgg gcattcacgg cgtgcctgcg gccgacaaaa agtacagcat cggccttgat  120
atcggcacca atagcgtggg ctgggccgtt atcacagacg aatacaaggt acccagcaag  180
aagttcaagg tgctggggaa tacagacagg cactctatca gaaaaacct tatcggggct  240
ctgctgtttg actcaggcga gaccgccgag gccaccagat tgaagagac cgcaaggcga  300
aggtacaccc ggaggaagaa caggatctgc tatctgcagg agatcttcag caacgagatg  360
gccaaggtgg acgacagctt cttccacagg ctggaggaga gcttccttgt cgaggaggat  420
aagaagcacg aacgacaccc catcttcggc aacatagtcg acgaggtcgc ttatcacgag  480
aagtacccca ccatctacca cctgcgaaag aaattggtgg atagcaccga taagccgac  540
ttgcgactta tctacttggc tctggcgcac atgattaagt tcaggggcca cttcctgatc  600
```

-continued

```
gagggcgacc ttaacccgga caacagtgac gtagacaaat tgttcatcca gcttgtacag  660
acctataacc agctgttcga ggaaaaccct attaacgcca gcggggtgga tgcgaaggcc  720
atacttagcg ccaggctgag caaaagcagg cgcttggaga acctgatagc ccagctgccc  780
ggtgaaaaga agaacggcct cttcggtaat ctgattgccc tgagcctggg cctgacccca  840
aacttcaaga gcaacttcga cctggcagaa gatgccaagc tgcagttgag taaggacacc  900
tatgacgacg acttggacaa tctgctcgcc caaatcggcg accagtacgc tgacctgttc  960
ctcgccgcca agaacctttc tgacgcaatc ctgcttagcg atatccttag ggtgaacaca 1020
gagatcacca aggcccccct gagcgccagc atgatcaaga ggtacgacga gcaccatcag 1080
gacctgaccc ttctgaaggc cctggttgagg cagcaactgc ccgagaagta caaggagatc 1140
tttttcgacc agagcaagaa cggctacgcc ggctacatcg acggcgggagc cagccaagag 1200
gagttctaca agttcatcaa gcccatcctg gagaagatgg atggcaccga ggagctgctg 1260
gtgaagctga cagggaaga tttgctccgg aagcagagga cctttgacaa cggtagcatc 1320
ccccaccaga tccacctggg cgagctgcac gcaaatactga ggcgacagga ggattctac 1380
cccttcctca aggacaatag ggagaaaatc gaaaagattc tgaccttcag gatcccctac 1440
tacgtgggcc ctcttgccag gggcaacagc cgattcgctt ggatgacaag aaagagcgag 1500
gagaccatca ccccctggaa cttcgaggaa gtggtggaca aggagcaag cgcgcagtct 1560
ttcatcgaac ggatgaccaa tttcgacaaa aacctgccta cgagaaggt gctgcccaag 1620
cacagcctgc tttacgagta cttcaccgtg tacaacgagc tcaccaaggt gaaatatgtg 1680
accgagggca tgcgaaaacc cgcttttcctg agcggcgagc agaagaaggc catcgtggac 1740
ctgctgttca agaccaacag gaaggtgacc gtgaagcagc tgaaggagga ctacttcaag 1800
aagatcgagt gctttgatag cgtggaaata agcggcgtgg aggacaggtt caacgccagc 1860
ctgggcaacct accacgactt gttgaagata atcaaagaca aggatttcct ggataatgaa 1920
gagaacgagg atatactcga ggacatcgtg ctgactttga ccctgtttga ggaccgagag 1980
atgattgaag aaaggctcaa aacctacgcc cacctgttcg acgacaaagt gatgaaacaa 2040
ctgaagagac aagatacac cggctgggc agactgtcca ggaagctcat caacggcatt 2100
agggacaagc agagcggcaa gaccatcctg gatttcctga gtccgacgg cttcgccaac 2160
cgaaacttca tgcagctgat tcacgatgac agcttgacct tcaaggagga catccagaag 2220
gcccaggtta gcgccagggg cgactccctg cacgaacata ttgcaaacct ggcaggctcc 2280
cctgcgatca agagggcat actgcagacc gttaaggttg tggacgaatt ggtcaaggtc 2340
atgggcagcc acaagcccga aaacatagtt atagagatgg ccagagagaa ccagaccacc 2400
caaaagggcc agaagaacag ccgggagcgc atgaaaagga tcgaggaggg tatcaaggaa 2460
ctcggaagcc agatcctcaa agagcacccc gtgagaata cccagctcca gaacgagaag 2520
ctgtacctgt actacctgca gaacggcagg gacatgtacg ttgaccagga gttggacatc 2580
aacaggcttt cagactatga cgtggatcac atagtgcccc agagcttcct taaagacgat 2640
agcatcgaca acaaggtcct gacccgctcc gacaaaaaca ggggcaaaag cgacaacgtg 2700
ccaagcgaag aggtggttaa aaagatgaag aactactgga ggcaactgct aacgcgaaaa 2760
ttgatcaccc agaaaagtt cgataacctg accaaggccg agagggcgg actctccgaa 2820
cttgacaaag cgggcttcat aaagaggcag ctggtcgaga cccgacagat cacgaagcac 2880
gtggcccaaa tcctcgacag cagaatgaat accaagtacg atgagaatga caactcatc 2940
agggaagtga agtgattac cctgaagagc aagttggtgt ccgactttcg caaagatttc 3000
cagttctaca aggtgaggga gatcaacaac taccaccatg cccacgacgc atacctgaac 3060
gccgtggtcg gcaccgccct gattaagaag tatccaaagc tggagtccga atttgtctac 3120
ggcgactaca aggtttacga tgtgaggaag atgatcgcta agagcgaaca ggagatcggc 3180
aaggccaccg ctaagtattt cttctacagc aacatcatga acttttttcaa gaccgagatc 3240
acacttgcca acggcgaaat caggaagagg ccgcttatcg agaccaacgg tgagaccggc 3300
gagatcgtgt gggacaaggg cagggacttc gccaccgtga ggaaagtcct gagcatgccc 3360
caggtgaata ttgtgaaaaa aactgaggtg cagacagggc gcttagcaa ggaatccatc 3420
ctgcccaaga ggaacagcga caagctgatc gcccggaaga aggactggga ccctaagaag 3480
tatgaggct cgacagccc caccgtagcc tacagcgtgc tggtggtcgc gaaggtagag 3540
aagggggaaga gcaagaaact gaagagcgtg aaggagctgc tcggcataac catcatggag 3600
aggtccagct ttgagaagaa ccccattgac ttttttgagg ccaagggcta caaagaggtc 3660
aaaaaggacc tgatcatcaa actccccaag tactccctgt ttgaattgga gaacggcaga 3720
aagaggatgc tggcgagcgc tggggaactg caaaagggca cgaactggc gctgcccagc 3780
aagtacgtga ttttctgta cctggcgtcc cactacgaaa agctgaaagg cagccccgag 3840
gacaacgagc agaagcagct gttcgtggag cagcacaagc attacctgga cgagataatc 3900
gagcaaatca gcgagttcag caagaggggtg attctggccg acgcgaacct ggataaggtc 3960
ctcagcgcct acaacaagca ccgagacaaa cccatcaggg agcaggccga gaatatcata 4020
cacctgttca ccctgacaaa tctgggcgca cctgcggcat tcaaatactt cgataccacc 4080
atcgacagga aaaggtacac tagcactaag gaggtgctgg atgccacctt gatccaccag 4140
tccattaccg gcctgtatga gaccaggatc gacctgagcc agcttggagg cgactctagg 4200
gcggacccaa aaaagaaaag gaaggtggaa ttccaccaca ctggactagt ggatccgagc 4260
tcggtaccaa gcttaagttt aaaccgctga                                   4290
```

```
SEQ ID NO: 4          moltype = AA  length = 1368
FEATURE               Location/Qualifiers
REGION                1..1368
                      note = SYNTHETIC
source                1..1368
                      mol_type = protein
                      organism = synthetic construct
SEQUENCE: 4
MDKKYSIGLD IGTNSVGWAV ITDEYKVPSK KFKVLGNTDR HSIKKNLIGA LLFDSGETAE   60
ATRLKRTARR RYTRRKNRIC YLQEIFSNEM AKVDDSFFHR LEESFLVEED KKHERHPIFG  120
NIVDEVAYHE KYPTIYHLRK KLVDSTDKAD LRLIYLALAH MIKFRGHFLI EGDLNPDNSD  180
VDKLFIQLVQ TYNQLFEENP INASGVDAKA ILSARLSKSR RLENLIAQLP GEKKNGLFGN  240
LIALSLGLTP NFKSNFDLAE DAKLQLSKDT YDDDLDNLLA QIGDQYADLF LAAKNLSDAI  300
LLSDILRVNT EITKAPLSAS MIKRYDEHHQ DLTLLKALVR QQLPEKYKEI FFDQSKNGYA  360
GYIDGGASQE EFYKFIKPIL EKMDGTEELL VKLNREDLLR KQRTFDNGSI PHQIHLGELH  420
AILRRQEDFY PFLKDNREKI EKILTFRIPY YVGPLARGNS RFAWMTRKSE ETITPWNFEE  480
```

```
VVDKGASAQS FIERMTNFDK NLPNEKVLPK HSLLYEYFTV YNELTKVKYV TEGMRKPAFL    540
SGEQKKAIVD LLFKTNRKVT VKQLKEDYFK KIECFDSVEI SGVEDRFNAS LGTYHDLLKI    600
IKDKDFLDNE ENEDILEDIV LTLTLFEDRE MIEERLKTYA HLFDDKVMKQ LKRRYTGWG    660
RLSRKLINGI RDKQSGKTIL DFLKSDGFAN ANFMQLIHDD SLTFKEDIQK AQVSGQGDSL    720
HEHIANLAGS PAIKKGILQT VKVVDELVKV MGRHKPENIV IEMARENQTT QKGQKNSRER    780
MKRIEEGIKE LGSQILKEHP VENTQLQNEK LYLYYLQNGR DMYVDQELDI NRLSDYDVDH    840
IVPQSFLKDD SIDNKVLTRS DKNRGKSDNV PSEEVVKKMK NYWRQLLNAK LITQRKFDNL    900
TKAERGGLSE LDKAGFIKRQ LVETRQITKH VAQILDSRMN TKYDENDKLI REVKVITLKS    960
KLVSDFRKDF QFYKVREINN YHHAHDAYLN AVVGTALIKK YPKLESEFVY GDYKVYDVRK    1020
MIAKSEQEIG KATAKYFFYS NIMNFFKTEI TLANGEIRKR PLIETNGETG EIVWDKGRDF    1080
ATVRKVLSMP QVNIVKKTEV QTGGFSKESI LPKRNSDKLI ARKKDWDPKK YGGFDSPTVA    1140
YSVLVVAKVE KGKSKKLKSV KELLGITIME RSSFEKNPID FLEAKGYKEV KKDLIIKLPK    1200
YSLFELENGR KRMLASAGEL QKGNELALPS KYVNFLYLAS HYEKLKGSPE DNEQKQLFVE    1260
QHKHYLDEII EQISEFSKRV ILADANLDKV LSAYNKHRDK PIREQAENII HLFTLTNLGA    1320
PAAFKYFDTT IDRKRYTSTK EVLDATLIHQ SITGLYETRI DLSQLGGD               1368

SEQ ID NO: 5              moltype = DNA  length = 4251
FEATURE                   Location/Qualifiers
misc_feature              1..4251
                          note = SYNTHETIC
source                    1..4251
                          mol_type = other DNA
                          organism = synthetic construct
SEQUENCE: 5
atgggcagca gcgccccaaa gaagaagcgg aaggtcggta tccacggagt cccagcagcc    60
atggacaaaa agtactctat tggcctggat atcgggacca acagcgtcgg gtgggctgtt    120
atcaccgacg agtataaagt accttcgaaa aagttcaaag tgctgggcaa caccgatcgc    180
cattcaatca aaaagaactt gattggtgcg ctgttgtttg actccgggga aaccgccgag    240
gcgactcgcc ttaaacgtac agcacgtcgc cggtacactc ggcgtaagaa tcgcatttgc    300
tatttgcagg aaatctttag caacgagatg gcaaaagtgc atgactcgtt tttccaccgc    360
ctcgaggaaa gctttctggt ggaggaagac aaaaagcatg agcgtcaccc gatcttcggc    420
aacattgtcg atgaagtagc gtatcatgaa aaatacccaa ccatttacca cttacgcaaa    480
aagctggtgg acagcactga caaagctgat tgcgcctta tctatttagc cctggcacat    540
atgattaagt ttcgtggtca cttcctgatc gaaggagact taaatcccga caacagtgat    600
gttgataaat tgtttattca gcttgtccaa acttacaatc aactgttcga ggaaaacccg    660
atcaatgcct ccggtgtgga tgcaaaagcc attttaagtg cacgccttag caagtcccgt    720
cgcttagaaa accttatcgc gcagctgccc ggcgagaaaa agaatggttt gtttgggaac    780
cttattgcct tgagcttagg cctcaccccg aatttcaaaa gtaatttcga tcttgcagaa    840
gacgccaaat tacaactgtc gaaggatact tatgatgacg atctcgataa tctgttagcg    900
cagattggtg accaatacgc cgatctttt ctggcggcta aaaatctgag cgacgccatc    960
ttgctttcgg atattctccg cgttaacacc gaaatcacga agcgcctct tagtgccagc    1020
atgattaaac gttatgatga acaccaccag gacctgacct tactcaaagc gttggttcgc    1080
cagcaactgc cagagaagta caaagaaatc ttctttgatc agtcaaagaa tggttatgcc    1140
ggctatattg acgggggtgc aagccaagag gaattctaca aatttatcaa gcctattctg    1200
gagaaaatgg atggcaccga agagttattg gtgaagctta accgtgaaga cctcctgcgg    1260
aaacagcgca cattcgataa tggttcgatc ccacaccaaa tccatttggg ggagttacac    1320
gctattttgc gtcgccagga agacttttac cctttcctga aggataaccg agagaaaatt    1380
gagaagatcc ttacctttcg tattccgtat tacgtaggcc ccttagcacg gggtaatagc    1440
cgtttcgcgt ggatgacacg gaagtcggaa gagacgatca cccgtgggaa cttcgaagag    1500
gtagtcgaca agggcgcatc agcgcagtct tttattgaac gtatgacgaa tttcgataaa    1560
aacttgccca atgagaaggt gcttccgaaa cattccttgt tatatgaata ttttacagtt    1620
tacaacgagc tgaccaaggt taaatacgtg acggaaggaa tgcgcaagcc cgcttttctt    1680
agcggtgagc aaaaaaaggc gatcgtcgac ctgttattca aaacgaatcg taaggtgact    1740
gtaaagcaac tcaaagaaga ttacttcaaa aagattgagt gcttcgacag cgtcgaaatc    1800
tctggggtag aggatcggtt taacgcaagt ttaggtacct accatgacct gcttaaaatc    1860
attaaggata aagacttctt agataatgaa gagaacgaag atattctcga ggacatcgtc    1920
ttgacgttaa cctatttga ggatcgtgaa atgattgagg aacgcctcaa aacttatgcc    1980
cacctgttcg acgataaggt gatgaagcag ctgaaacgtc ggcgctacac aggatggggc    2040
cgcttgagtc gcaaacttat taacgcaatc cgtgacaagc aatccggcaa aacgattctg    2100
gatttcttga gtcggacggg atttgctaat gcgaacttca tgcagttgat ccatgatgac    2160
tccctgactt ttaaagagga tattcaaaag gcgcaggtta gtggtcaagg cgacagctta    2220
cacgaacaca tcgcaatttt ggctggttcg ccggccatta aaagggggat cctcagacc    2280
gtgaaagttt agatgagct tgttaaggtc atgggtcgtc ataagcccga aacatcgtg    2340
attgaaatgg cgcgggagaa tcaaacgacc cagaaggaca aaagaatag ccgtgaacgg    2400
atgaagcgga tcgaggaagg cattaaagag ctggggtctc aaatcttgaa ggaacaccct    2460
gtggagaaca ctcagctcca aaatgaaaaa cttttacctgt actatttgca gaacggacgc    2520
gatatgtacg tggaccaaga gttggatatt aatcggctga gtgactacga cgttgatcat    2580
atcgtcccgc agagcttcct caaagacgat tctattgaca ataaggtact gacgcgctct    2640
gataaaaacc gtggtaagtc ggacaacgtg ccctccgaag aggttgtgaa aaagatgaaa    2700
aattattggc gccagctttt aaacgcgaag ctgatcacac aacgtaaatt cgataatttg    2760
accaaggctg aacggggtgg cctgagcgag ttagataagg caggatttat taacgccag    2820
ttagtggaga ctcgtcaaat caccaaacat gtcgcgcaga ttttgacag ccggatgaac    2880
accaagtacg atgaaaatga caaactgatc cgtgaggtga agtcattac tctgaagtcc    2940
aaattagtta tgatttccg gaaggacttt caattctaa agtccgtga aattaataac    3000
tatcatcacg cacatgacgc gtacctgaat gcagtggttg gaccgccct tatcaagaaa    3060
tatcctaagc tggagtcgga gttttgtctat ggcgactata aggtatacga tgttcgcaaa    3120
atgattgcga aatctgagca ggagatcggt aaggcaaccg caaaatattt cttttactca    3180
aacattatga atttctttaa gacagaaatc actctgccaa cggggagat cgcaaacgt    3240
ccgttgatcg aaacaaacgg cgagactggc gaaattgttt gggacaaagg cgtgattc    3300
```

```
gcgacggtgc gcaaggtact gagcatgcct caagtcaata ttgttaagaa aaccgaagtg    3360
cagacgggcg ggttttccaa ggaaagcatc ttacccaaac gtaattcaga taaacttatt    3420
gcacgcaaaa aggactggga tccgaaaaag tatggaggct tcgacagtcc aaccgtagcc    3480
tactctgttc tcgttgtagc gaaagtagaa aagggtaaat ccaagaaact gaaatctgtc    3540
aaggagttgc ttggaatcac cattatggag cgtagctcct tcgagaagaa cccgattgac    3600
tttctggaag ccaaaggata taagaggtc aagaaagatc ttatcattaa gctgcctaag     3660
tattcactct tcgagctgga aaatggtcgt aaacgcatgc tcgcttctgc cggcgagttg    3720
cagaagggca atgaattagc acttccatca aagtacgtta acttcctgta tttggccagc    3780
cattacgaga aactgaaggg gtctccagag gacaacgaac agaaacaatt atttgtagag    3840
cagcacaagc attatcttga tgaaatcatt gagcaaattt ccgaattcag taaacgcgta    3900
atcctggccg atgcaaacct cgacaaggtg ctgagcgctt acaataagca tcgcgacaaa    3960
cctatccgtg agcaggctga aaatatcatt cacctgttca cattaacgaa cctgggcgct    4020
ccggccgctt ttaaatattt cgacacgaca atcgaccgta agcgctatac cagtacgaaa    4080
gaagtgtttg atgcgaccct tattcaccag tcaattacag gattatatga gaccgtactg    4140
gaccttagcc aattaggtgg ggatgcggcc ccgaagaaaa aacgcaaagt ggatccgaag    4200
aaaaaacgca aagtggcggc cgcactcgag caccaccacc accaccactg a             4251

SEQ ID NO: 6              moltype = DNA   length = 4290
FEATURE                   Location/Qualifiers
misc_feature              1..4290
                          note = SYNTHETIC
source                    1..4290
                          mol_type = other DNA
                          organism = synthetic construct
SEQUENCE: 6
atgggcaagc ccatccctaa ccccctgttg gggctggaca gcaccgctcc caaaaagaaa    60
aggaaggtgg gcattcacgg cgtgcctgcg gccgacaaaa agtacagcat cggccttgat    120
atcggcacca atagcgtggg ctgggccgtt atcacagacg aatacaaggt acccagcaag    180
aagttcaagg tgctggggaa tacagacagg cactctatca agaaaaacct tatcgggct     240
ctgctgtttg actcaggcga gaccgccgag gccaccaggt tgaagaggac cgcaaggcga    300
aggtacaccc ggaggaagaa caggatctgc tatctgcagg agatcttcag caacgagatg    360
gccaaggtgg acgacagctt cttccacagg ctggaggaga gcttccttgt cgaggaggat    420
aagaagcacg aacgacaccc catcttcggc aacatagtcg acgaggtcgc ttatcacgag    480
aagtaccca catctacca cctgcgaaag aaattggtgg atagcaccga taaagccgta    540
ttgcgactta tctacttggc tctgcgcac atgattaagt tcaggggcca cttcctgatc    600
gagggcgacc ttaaccccga caacagtgac gtagacaaat tgttcatcca gcttgtacag    660
acctataacc agctgttcga ggaaaaccct attaacgcca gcggggtgga tgcgaaggcc    720
atacttagcg ccaggctgag caaaagcagg cgcttggaga acctgatagc ccagctgccc    780
ggtgaaaaga agaacggcct cttcggtaat ctgattgccc tgagcctggg cctgacccc     840
aacttcaaga gcaacttcga cctggcagaa gatgccaagc tgcagttgag taaggacacc    900
tatgacgacg acttggacaa tctgctcgcc caaatcggcg accagtacgc tgacctgttc    960
ctcgccgcca gaaccttttc tgacgcaatc ctgcttagcg atatccttag ggtgaacaca    1020
gagatcacca aggccccct gagcgccagc atgatcaaga ggtacgacga gcaccatcag    1080
gacctgaccc ttctgaaggc cctggtgagg cagcaactgc ccgagaagta caaggagatc    1140
ttttttgacc agagcaagaa cggctacgcc ggctacatcg acggcggagc cagccaagag    1200
gagttctaca gttcatcaa gcccatcctg gagaagatgg atggcaccga ggagctgctg    1260
gtgaagctga acagggaaga tttgctccgg aagcagagga cctttgacaa cggtagcatc    1320
ccccaccaga tccacctggg cgagctgcac gcaatactga ggcgacagga ggatttctac    1380
cccttcctca aggacaatag ggagaaaatc gaaaagattc tgaccttcag gatccctac     1440
tacgtgggcc ctcttgccag gggcaacagc cgattcgctt ggatgacaag aaagagcgag    1500
gagaccatca ccccctggaa cttcgaggaa gtggtgacaa aaggagcgag gcgcagtct     1560
ttcatcgaac ggatgaccaa tttgacaaa aacctgccta acgagaaggt gctgcccaag    1620
cacagcctgc tttacgagta cttcaccgtg tacaacgagc tcaccaaggt gaaatatgtg    1680
accgagggca tgcgaaaacc cgcttttcctg agcggcgagc agaagaaggc catcgtggac    1740
ctgctgttca gaccaacag gaaggtgacc gtgaagcagc tactttcaag                1800
aagatcgagt gctttgatag cgtggaaata agcggcgtgg aggacaggtt caacgccagc    1860
ctgggcaccT accacgactt gttgaagata atcaaagaca aggattcct ggataatgag     1920
gagaacgagg atatactcga ggacatcgtg ctgactttga ccctgtttga ggaccgagag    1980
atgattgaag aaaggctcaa aacctacgcc cacctgttcg acgacaaagt gatgaaacaa    2040
ctgaagagac gaagatacac cggctgggc agactgtcca gaagctcat caacggcatt     2100
agggacaagc agagcggcaa gaccatcctg gatttcctga gtccgacgg cttcgccaac    2160
gccaacttca tgcagctgat tcacgatgac agcttgacct tcaaggagga catccagaag    2220
gcccaggtta gcggccaggg cgactccctg cacgaacata ttgcaaacct ggcaggctcc    2280
cctgcgatca gaaagggcat actgcagacc gttaaggtg tggtcaaggtc                2340
atgggcaggc acaagcccga aaacatagtt atagagatgc cagagaaa ccagaccacc       2400
caaaagggcc agaagaacag ccgggagcgc atgaaaagga tcgaggaggg tatcaaggaa    2460
ctcggaagcc agatcctcaa agagcacccc gtggagaata cccagctcca gaacgagaag    2520
ctgtacctgt actacctgca gaacggcagg gacatgtacg ttgaccagga gttggacatc    2580
aacaggctt cagactatga cgtggatcac atagtgcccc agagctttct taaagacgat    2640
agcatcgaca caaggtcct gacccgctcc gacaaaaaca gggcaaaag cgacaacgtg    2700
ccaagcgaag aggtggttaa aaagatgaag aactactgga ggcaactgct caacgcgaaa    2760
ttgatcaccc agaaaagtt cgataacctg accaaggccg agaggggcgg actctccgaa    2820
cttgacaaag cgggcttcat aaagaggcag ctggtcgaga cccgacagat cacgaagcac    2880
gtggcccaaa tcctcgacag cagaatgaat accaagtacg atgaaatgac ccactcatc    2940
agggaagtga aagtgattac cctgaagagc aagttggtgt ccgactttcg caaagatttc    3000
cagttctaca aggtgaggga gatcaacaac taccaccatg cccacgacgc atacctgaac    3060
gccgtggtcg gcaccgccct gattaagaag tatccaaagc tggagtccga atttgtctac    3120
ggcgactaca aagtttacga tgtgaggaag atgatcgcta gagcgaaca ggagatcggc    3180
aaggccaccg ctaagtattt cttctacagc aacatcatga actttttcaa gaccgagatc    3240
```

-continued

```
acacttgcca acggcgaaat caggaagagg ccgcttatcg agaccaacgg tgagaccggc   3300
gagatcgtgt gggacaaggg cagggacttc gccaccgtga ggaaagtcct gagcatgccc   3360
caggtgaata ttgtgaaaaa aactgaggtg cagacaggcg gctttagcaa ggaatccatc   3420
ctgcccaaga ggaacagcga caagctgatc gcccggaaga aggactggga ccctaagaag   3480
tatggaggct tcgacagccc caccgtagcc tacagcgtgc tggtggtcgc gaaggtagag   3540
aagggggaaga gcaagaaact gaagagcgtg aaggagctgc tcggcataac catcatggag   3600
aggtccagct ttgagaagaa ccccattgac tttttggaag ccaagggcta caaagaggtc   3660
aaaaaggacc tgatcatcaa actccccaag tactccctgt ttgaattgga gaacggcaga   3720
aagaggatgc tggcgagcgc tggggaactg caaaagggca acgaactggc gctgcccagc   3780
aagtacgtga attttctgta cctggcgtcc cactacgaaa agctgaaagg cagccccgag   3840
gacaacgagc agaagcagct gttcgtggag cagcacaagc attacctgga cgagataatc   3900
gagcaaatca gcgagttcag caagaggggtg attctggccg acgcgaacct ggataaggtc   3960
ctcagcgcct acaacaagca ccgagacaaa cccatcaggg agcaggccga gaatatcata   4020
cacctgttca ccctgacaaa tctgggcgca cctgcggcat tcaaatactt cgataccacc   4080
atcgacagga aaaggtacac tagcactaag gaggtgctgg atgccacctt gatccaccag   4140
tccattaccg gcctgtatga gaccaggatc gacctgagcc agcttggagg cgactctagg   4200
gcggacccaa aaaagaaaag gaaggtggaa ttccaccaca ctggactagt ggatccgagc   4260
tcggtaccaa gcttaagttt aaaccgctga                                     4290
```

MUTATIONS IN *Streptococcus pyogenes* Cas9 DISCOVERED BY BROAD SCANNING MUTAGENESIS DEMONSTRATE ENHANCEMENT OF DNA CLEAVAGE ACTIVITY

CROSS-REFERENCE TO RELATED APPLICATIONS

This application claims benefit of priority under 35 U.S.C. 119 to U.S. Provisional Patent Application Ser. No. 63/217,881, filed Jul. 2, 2021 and entitled "NOVEL MUTATIONS IN *STREPTOCOCCUS PYOGENES* CAS9 DISCOVERED BY BROAD SCANNING MUTAGENESIS DEMONSTRATE ENHANCEMENT OF DNA CLEAVAGE ACTIVITY," the contents of each application are herein incorporated by reference in its entirety.

SEQUENCE LISTING

The instant application contains a Sequence Listing that has been submitted in XML format via Patent Center and is hereby incorporated by reference in its entirety. The XML copy, created on Dec. 19, 2022, is named IDT01-020-US.XML, and is 28,282 bytes in size.

FIELD OF THE INVENTION

This invention pertains to Cas9 mutant genes, polypeptides encoded by the same and their use in compositions of CRISPR-Cas systems for improving on-site targeted cleavage activity.

BACKGROUND OF THE INVENTION

SpCas9 is an RNA-guided endonuclease utilizing the Clustered Regularly Interspaced Short Palindromic Repeat (CRISPR) adaptive immune system from *Streptococcus pyogenes*. Cas9 utilizes a RNA guide complementary to a 20 nucleotide DNA target sequence, commonly referred to as a protospacer. Critical to the recognition of correct DNA target for SpCas9 includes both crRNA and the canonical "NGG" protospacer adjacent motif (PAM), which is a 3-bp sequence immediately downstream of the protospacer. The Cas9-gRNA ribonucleoprotein (RNP) complex mediates double-stranded DNA breaks (DSBs), which are then repaired by either the non-homologous end joining (NHEJ, typically introduces mutations or indels at the cut site), or the homology directed repair (HDR) system for precise editing if a suitable template nucleic acid is present.

Currently, many point mutations have been identified to improve the specificity of SpCas9 to mitigate off-target editing, although at the significant cost of on-target potency[1]. However, for applications where off-target editing is less of a concern (such as high-throughput genetic screen), a high-activity SpCas9 with uniform editing efficiency across all targetable sites is desirable. In addition, while many SpCas9 variants with alternative PAM preference have been developed, their utilities are limited to the reduced on-target potency[3]. Increasing on-target activity of SpCas9 through mutagenesis may rescue the poor performance of these PAM variants in human cells when delivered as RNP. Further, it has been suggested that the on-target activity of SpCas9 is a rate-limiting step for advanced gene editing platforms established upon SpCas9, such base editing and prime editing.

Therefore, a need remains for methods to improve specificity of Cas9 genome editing. In particular, there exists a need to identify novel point mutations to enhance or increase on-target activity of SpCas9 to improve the performance of a variety of gene editing platforms that are widely adopted by the community[4]. This disclosure provides a solution to a long-felt need of generating novel point mutations to enhance on-target activity of SpCas9 that may improve the performance of a variety of gene editing platforms that are widely adopted by the community[4].

BRIEF SUMMARY OF THE INVENTION

This invention pertains to Cas9 mutant genes and polypeptides for use in CRISPR systems, and their methods of use.

In a first aspect, an isolated mutant Cas9 protein is provided. The isolated mutant Cas9 protein is active in a Clustered Regularly Interspaced Short Palindromic Repeats (CRISPR)/CRISPR-associated protein endonuclease system ("CRISPR/Cas endonuclease system"). The CRISPR/Cas endonuclease system displays increased on-target editing activity relative to a wild-type CRISPR/Cas endonuclease system.

In a second aspect, an isolated ribonucleoprotein (RNP) complex is provided. The RNP complex includes a mutant Cas9 protein and a gRNA complex. The isolated ribonucleoprotein complex is active as a CRISPR/Cas endonuclease system, wherein the resultant CRISPR/Cas endonuclease system displays increased on-target editing activity relative to a wild-type CRISPR/Cas endonuclease system.

In a third aspect, an isolated nucleic acid encoding a mutant Cas9 protein is provided. The mutant Cas9 protein is active in a CRISPR/Cas endonuclease system, wherein the CRISPR/Cas endonuclease system displays increased on-target editing activity relative to a wild-type CRISPR/Cas endonuclease system In a fourth aspect, a CRISPR/Cas endonuclease system is provided. The CRISPR/Cas endonuclease system includes a mutant Cas9 protein and a gRNA. The CRISPR/Cas endonuclease system displays increased on-target editing activity relative to a wild-type CRISPR/Cas endonuclease system.

In a fifth aspect, a method of performing gene editing having increased on-target editing activity is provided. The method includes the step of contacting a candidate editing DNA target site locus with an active CRISPR/Cas endonuclease system having a mutant Cas9 protein complexed with an appropriate gRNA (e.g., crRNA:tracrRNA complex or sgRNA). Said interaction can occur in any context, for example, in a live animal, in live cells, or in isolated DNA in vitro.

DETAILED DESCRIPTION OF THE INVENTION

Figure 1:
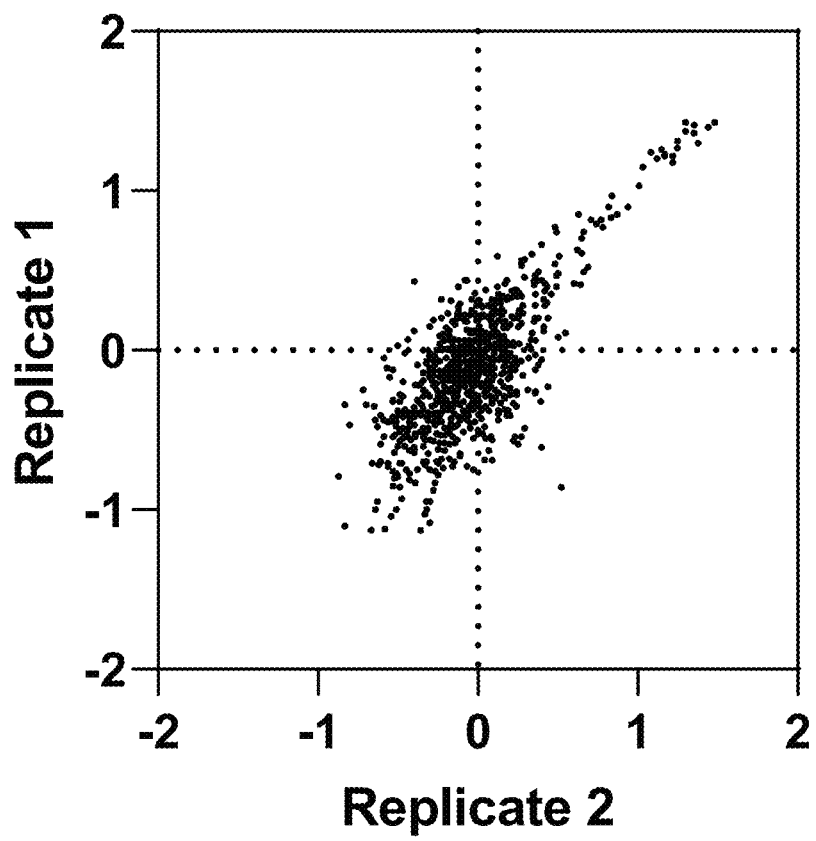
FIG. 1 depicts an exemplary Pearson Correlation of natural log scale enriched mutations replicate 1 and replicate 2. This figure shows good agreement between replicates and indicates a fraction of SpCas9 mutants with increased cleavage activity.

The methods and compositions of the invention described herein provide mutant SpyCas9 nucleic acids and polypeptides for use in a CRISPR-Cas system. The present invention describes novel Cas9 mutants that increased on-target editing activity relative to the wild-type protein. These and other advantages of the invention, as well as additional inventive features, will be apparent from the description of the invention provided herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The term "wild-type Cas9 protein" ("WT-Cas9" or "WT-Cas9 protein") encompasses a protein having the identical amino acid sequence of the naturally-occurring *Streptococcus pyogenes* Cas9 (e.g., SEQ ID NO:1) and that has biochemical and biological activity when combined with a suitable guide RNA (for example sgRNA or dual crRNA: tracrRNA compositions) to form an active CRISPR-Cas endonuclease system.

The term "wild-type CRISPR/Cas endonuclease system" refers to a CRISPR/Cas endonuclease system that includes wild-type Cas9 protein and a suitable gRNA.

The phrase "active CRISPR/Cas endonuclease system displays increased on-target editing activity relative to a wild-type CRISPR/Cas endonuclease system" refers to the activity of a CRISPR/Cas endonuclease system that includes a mutant Cas9 protein that displays an enhanced or increased on-target editing activities of a wild-type CRISPR/Cas endonuclease system that includes wild-type Cas9 protein of SEQ ID NO: 1 when both CRISPR/Cas endonuclease systems include the identical gRNA for a given target sequence. Preferred on-target activities of the CRISPR/Cas endonuclease systems depend upon the gRNA and the target sequence of interest; such preferred increased on-target activities of CRISPR/Cas endonuclease systems having mutant Cas9 proteins are illustrated in the herein.

The term "polypeptide" refers to any linear or branched peptide comprising more than one amino acid. Polypeptide includes protein or fragment thereof or fusion thereof, provided such protein, fragment or fusion retains a useful biochemical or biological activity.

Fusion proteins typically include extra amino acid information that is not native to the protein to which the extra amino acid information is covalently attached. Such extra amino acid information may include tags that enable purification or identification of the fusion protein. Such extra amino acid information may include peptides that enable the fusion proteins to be transported into cells and/or transported to specific locations within cells.

The term "isolated nucleic acid" include DNA, RNA, cDNA, and vectors encoding the same, where the DNA, RNA, cDNA and vectors are free of other biological materials from which they may be derived or associated, such as cellular components. Typically, an isolated nucleic acid will be purified from other biological materials from which they may be derived or associated, such as cellular components.

The term "isolated wild-type Cas9 nucleic acid" is an isolated nucleic acid that encodes a wild-type Cas9 protein. Examples of an isolated wild-type Cas9 nucleic acid include codon-optimized versions designed for efficient expression in *E. coli* or human cells, such as those nucleic acids encoded by SEQ ID NO: 2 and 3.

The term "isolated mutant Cas9 nucleic acid" is an isolated nucleic acid that encodes a mutant Cas9 protein, such as a Cas9 protein having an R691A mutation (SEQ ID NO: 4). Examples of an isolated mutant Cas9 nucleic acid include codon-optimized versions designed for efficient expression in *E. coli* or human cells, such as those nucleic acids encoded by SEQ ID NO: 5 and 6, respectively.

The term "length-modified," as that term modifies RNA, refers to a shortened or truncated form of a reference RNA lacking nucleotide sequences or an elongated form of a reference RNA including additional nucleotide sequences.

The term "chemically-modified," as that term modifies RNA, refers to a form of a reference RNA containing a chemically-modified nucleotide or a non-nucleotide chemical group covalently linked to the RNA. Chemically-modified RNA, as described herein, generally refers to synthetic RNA prepared using oligonucleotide synthesis procedures wherein modified nucleotides are incorporated during synthesis of an RNA oligonucleotide. However, chemically-modified RNA also includes synthetic RNA oligonucleotides modified with suitable modifying agents post-synthesis.

The term ALT-R®, as that term modifies an RNA (for example, such as a crRNA, a tracrRNA, a guide RNA, or a sgRNA), refers to an isolated, chemically synthesized, synthetic RNA.

The term ALT-R®, as that term modifies a protein (for example, such as a Cas9 protein), refers to an isolated, recombinant protein.

A competent CRISPR-Cas endonuclease system includes a ribonucleoprotein (RNP) complex formed with isolated Cas9 protein and isolated guide RNA selected from one of a dual crRNA:tracrRNA combination or a chimeric single-molecule sgRNA. In some embodiments, isolated length-modified and/or chemically-modified forms of crRNA and tracrRNA are combined with purified Cas9 protein, an isolated mRNA encoding Cas9 protein or a gene encoding Cas9 protein in an expression vector. In certain assays, isolated length-modified and/or chemically-modified forms of crRNA and tracrRNA can be introduced into cell lines that stably express Cas9 protein from an endogenous expression cassette encoding the Cas9 gene. In other assays, a mixture of length-modified and/or chemically-modified forms of crRNA and tracrRNA in combination with either mutant Cas9 mRNA or mutant Cas9 protein can be introduced into cells.

Mutant Cas9 Proteins Having Increased On-Target Gene Editing Activity

In a first aspect, an isolated mutant Cas9 protein is provided. The isolated mutant Cas9 protein is active in a Clustered Regularly Interspaced Short Palindromic Repeats (CRISPR)/CRISPR-associated protein endonuclease system ("CRISPR/Cas endonuclease system"). The resultant CRISPR/Cas endonuclease system displays increased on-target editing activity relative to a wild-type CRISPR/Cas endonuclease system.

A bacterial-based directed evolution of SpCas9 was performed to identify mutations with enhanced cleavage activity. A deep-scanning mutagenesis library containing all possible point mutations on the amino acid level over positions 1-75 of SpCas9 was initially created, with most clones containing only one mutation[2]. This type of library allows one to directly evaluate the phenotype of each point mutation, by measuring their relative survival rates over the wild-type (WT) protein in the bacterial screen. Since SpCas9 activity is generally very high in *E. coli*, a crRNA and target site with mismatches was selected to down-tune the cleavage activity, thereby creating a suitable selection pressure to identify mutant with enhanced activity (Table 1).

TABLE 1

RNA guides used for Cas9 screen.
Mismatch guide used for selection
in comparison to WT-guide RNA.

| | |
|---|---|
| Perfect Match | GGTGAGTGAGTGTGTGCGTG |
| MM7 | GGCCAGTGAGTGTGTGCGTG |
| MM15 | GGTGCCCGAGTGTGTGCGTG |

To identify high-activity mutant, the screening strain harboring the toxin plasmid was transformed with SpCas9 library and mismatched crRNA targeting a single site on the toxin plasmid. After recovery and induction, cells were plated on selective media with induction and incubated at 37° C. overnight. SpCas9 expression plasmids carried by the surviving *E. coli* cells were extracted and purified. Both input and selected plasmid libraries were sequenced with NGS to determine the frequencies of mutations at each position of SpCas9 in both libraries. The relative survival rate of each point mutation was calculated as the ratio of normalized frequency between selected and input library. Since the degree of cell survival under selection is indicative of the cleavage activity of SpCas9, any variants that are enriched during the selection over WT would be those with enhanced activity.

Figure 2:
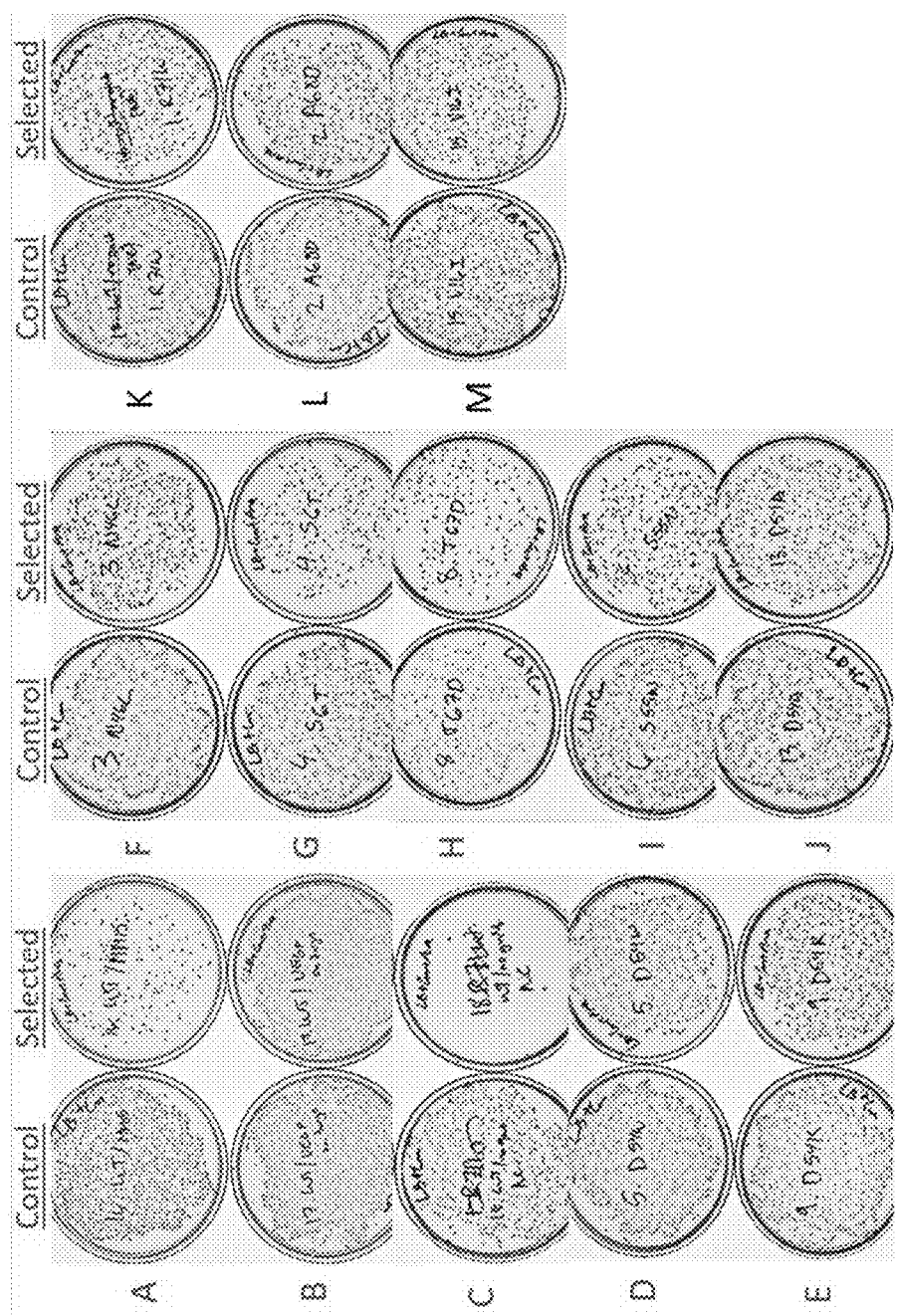
FIG. 2 depicts examples of individual novel SpCas9 mutations that enhance DNA cleavage utilizing mismatched guide RNA. The cleavage assay shows a validation of the initial screening process in which mutants show higher survival rates under selection than Wild-Type SpCas9. Survival of *E. coli* was dependent on the ability of Cas9 to cleave the intended target site on the toxin-encoding plasmid. Panels A-M depict Wild-Type SpCas9 plasmid with 'mismatch 15' guide RNA (A); Wild-Type SpCas9 with perfectly-matched guide RNA (B); Wild-Type SpCas9 plasmid with no guide RNA (C): Panels D-M: SpCas9 polypeptides having mutant single amino acid mutations identified from mutagenesis screen with 'mismatch 15' guide RNA: SpCas9 D54W (D); SpCas9 D54K (E); SpCas9 N46L (F); SpCas9 S6T (G); SpCas9 T67D (H); SpCas9 S55N (I); SpCas9 D54A (J); SpCas9 R71W (K); SpCas9 A68D (L); and SpCas9 V16I (M).

Table 2 and FIG. 1 summarize the phenotype of 266 point mutations of SpCas9 in the bacterial screen measuring the cleavage activity with a mismatched gRNA. Three biological replicates were performed with high consistency, which enabled us to confidently isolate a large collection of novel SpCas9 variants with enhanced activity. We therefore selectively validated several candidates in the context of *E. coli* cleavage assay. Individual mutant plasmid was cloned and delivered to screening *E. coli* strain in the presence of mismatched gRNA. Multiple novel SpCas9 mutants displayed significant improvement of DNA cleavage in *E. coli* over wild-type protein, which is indicated by a substantial increase of survival rate upon selection (FIG. 2). These results suggest the result of our high-throughput screen is highly accurate, which provided a large pool of candidates for further validation in the context of human cells.

TABLE 2

Point mutations enriched over WT SpCas9 (SEQ ID NO: 1). Shown in natural log, phenotype enrichment scores demonstrate point mutations of improving Cas9 activity.

| Number | Mutation | Position | Wild-Type Residue | Mutation Residue | Average | Standard Deviation |
|---|---|---|---|---|---|---|
| 1 | D54W | 54 | D | W | 1.53 | 0.06 |
| 2 | D54Y | 54 | D | Y | 1.45 | 0.02 |
| 3 | D54F | 54 | D | F | 1.39 | 0.10 |
| 4 | D54C | 54 | D | C | 1.37 | 0.05 |
| 5 | D54K | 54 | D | K | 1.36 | 0.08 |
| 6 | D54A | 54 | D | A | 1.36 | 0.05 |
| 7 | D54R | 54 | D | R | 1.31 | 0.04 |
| 8 | D54T | 54 | D | T | 1.31 | 0.07 |
| 9 | D54V | 54 | D | V | 1.28 | 0.04 |
| 10 | D54P | 54 | D | P | 1.27 | 0.12 |
| 11 | D54L | 54 | D | L | 1.26 | 0.06 |
| 12 | D54H | 54 | D | H | 1.19 | 0.12 |
| 13 | D54M | 54 | D | M | 1.17 | 0.05 |
| 14 | D54I | 54 | D | I | 1.17 | 0.10 |
| 15 | D54S | 54 | D | S | 1.17 | 0.03 |
| 16 | D54Q | 54 | D | Q | 1.13 | 0.09 |
| 17 | D54N | 54 | D | N | 1.05 | 0.08 |
| 18 | S55N | 55 | S | N | 1.02 | 0.07 |
| 19 | F53R | 53 | F | R | 0.97 | 0.04 |
| 20 | N14A | 14 | N | A | 0.93 | 0.12 |
| 21 | V16I | 16 | V | I | 0.92 | 0.04 |
| 22 | D54G | 54 | D | G | 0.87 | 0.01 |
| 23 | S55H | 55 | S | H | 0.84 | 0.15 |
| 24 | D54E | 54 | D | E | 0.82 | 0.07 |
| 25 | F53I | 53 | F | I | 0.80 | 0.03 |
| 26 | A68D | 68 | A | D | 0.78 | 0.08 |
| 27 | S55G | 55 | S | G | 0.74 | 0.04 |
| 28 | T67D | 67 | T | D | 0.70 | 0.23 |
| 29 | N14G | 14 | N | G | 0.70 | 0.12 |
| 30 | F53Y | 53 | F | Y | 0.69 | 0.09 |
| 31 | A68W | 68 | A | W | 0.68 | 0.07 |
| 32 | F53S | 53 | F | S | 0.65 | 0.04 |
| 33 | A68N | 68 | A | N | 0.65 | 0.10 |
| 34 | S55A | 55 | S | A | 0.64 | 0.16 |
| 35 | F53A | 53 | F | A | 0.60 | 0.01 |
| 36 | F53H | 53 | F | H | 0.60 | 0.15 |
| 37 | N46L | 46 | N | L | 0.59 | 0.16 |
| 38 | V16T | 16 | V | T | 0.58 | 0.13 |
| 39 | F53T | 53 | F | T | 0.58 | 0.08 |
| 40 | A68K | 68 | A | K | 0.55 | 0.02 |
| 41 | T67C | 67 | T | C | 0.52 | 0.09 |
| 42 | A68R | 68 | A | R | 0.49 | 0.06 |

TABLE 2-continued

Point mutations enriched over WT SpCas9 (SEQ ID NO: 1). Shown in natural log, phenotype enrichment scores demonstrate point mutations of improving Cas9 activity.

| Number | Mutation | Position | Wild-Type Residue | Mutation Residue | Average | Standard Deviation |
|---|---|---|---|---|---|---|
| 43 | K33G | 33 | K | G | 0.47 | 0.47 |
| 44 | F53P | 53 | F | P | 0.44 | 0.05 |
| 45 | A19V | 19 | A | V | 0.44 | 0.21 |
| 46 | L35G | 35 | L | G | 0.43 | 0.07 |
| 47 | T58H | 58 | T | H | 0.43 | 0.08 |
| 48 | S6T | 6 | S | T | 0.43 | 0.20 |
| 49 | L35P | 35 | L | P | 0.43 | 0.17 |
| 50 | I48L | 48 | I | L | 0.42 | 0.19 |
| 51 | A68L | 68 | A | L | 0.42 | 0.06 |
| 52 | K30S | 30 | K | S | 0.41 | 0.04 |
| 53 | N46K | 46 | N | K | 0.41 | 0.22 |
| 54 | R71L | 71 | R | L | 0.40 | 0.10 |
| 55 | K33S | 33 | K | S | 0.40 | 0.09 |
| 56 | F53N | 53 | F | N | 0.40 | 0.02 |
| 57 | F53V | 53 | F | V | 0.40 | 0.06 |
| 58 | I43C | 43 | I | C | 0.39 | 0.15 |
| 59 | T67Y | 67 | T | Y | 0.39 | 0.22 |
| 60 | T67M | 67 | T | M | 0.38 | 0.03 |
| 61 | L52D | 52 | L | D | 0.38 | 0.14 |
| 62 | R71W | 71 | R | W | 0.37 | 0.20 |
| 63 | F53L | 53 | F | L | 0.36 | 0.09 |
| 64 | L35T | 35 | L | T | 0.35 | 0.15 |
| 65 | N46D | 46 | N | D | 0.33 | 0.15 |
| 66 | T22V | 22 | T | V | 0.33 | 0.08 |
| 67 | K30R | 30 | K | R | 0.33 | 0.20 |
| 68 | N37A | 37 | N | A | 0.33 | 0.17 |
| 69 | L52C | 52 | L | C | 0.32 | 0.31 |
| 70 | K65M | 65 | K | M | 0.31 | 0.17 |
| 71 | F53M | 53 | F | M | 0.30 | 0.22 |
| 72 | F53G | 53 | F | G | 0.30 | 0.09 |
| 73 | K30L | 30 | K | L | 0.28 | 0.13 |
| 74 | R40P | 40 | R | P | 0.28 | 0.08 |
| 75 | T67G | 67 | T | G | 0.28 | 0.20 |
| 76 | T67I | 67 | T | I | 0.26 | 0.15 |
| 77 | S55R | 55 | S | R | 0.26 | 0.15 |
| 78 | K3S | 3S | K | S | 0.26 | 0.10 |
| 79 | L64H | 64 | L | H | 0.25 | 0.35 |
| 80 | E60H | 60 | E | H | 0.25 | 0.41 |
| 81 | A68S | 68 | A | S | 0.25 | 0.10 |
| 82 | K30W | 30 | K | W | 0.25 | 0.36 |
| 83 | T22W | 22 | T | W | 0.24 | 0.05 |
| 84 | K4P | 4P | K | p | 0.23 | 0.09 |
| 85 | S29W | 29 | S | W | 0.23 | 0.14 |
| 86 | K3Q | 3 | K | Q | 0.23 | 0.30 |
| 87 | S42I | 42 | S | I | 0.23 | 0.14 |
| 88 | L47M | 47 | L | M | 0.23 | 0.20 |
| 89 | S42V | 42 | S | V | 0.22 | 0.06 |
| 90 | K33F | 33 | K | F | 0.22 | 0.28 |
| 91 | N46T | 46 | N | T | 0.22 | 0.41 |
| 92 | K4E | 4E | K | E | 0.22 | 0.25 |
| 93 | Y72W | 72 | Y | W | 0.21 | 0.29 |
| 94 | K26Q | 26 | K | Q | 0.21 | 0.24 |
| 95 | D39K | 39 | D | K | 0.21 | 0.15 |
| 96 | T22I | 22 | T | I | 0.21 | 0.19 |
| 97 | T67S | 67 | T | S | 0.21 | 0.12 |
| 98 | N37T | 37 | N | T | 0.21 | 0.18 |
| 99 | K4Y | 4 | K | Y | 0.21 | 0.12 |
| 100 | I7Ter | 7 | I | r | 0.21 | 0.33 |
| 101 | K4A | 4A | K | A | 0.21 | 0.33 |
| 102 | K44M | 44 | K | M | 0.20 | 0.21 |
| 103 | K33Q | 33 | K | Q | 0.20 | 0.22 |
| 104 | T67W | 67 | T | W | 0.20 | 0.19 |
| 105 | T38A | 38 | T | A | 0.20 | 0.32 |
| 106 | F53K | 53 | F | K | 0.19 | 0.07 |
| 107 | F53W | 53 | F | W | 0.19 | 0.23 |
| 108 | I43M | 43 | I | M | 0.19 | 0.11 |
| 109 | L52N | 52 | L | N | 0.19 | 0.03 |
| 110 | T67Q | 67 | T | Q | 0.18 | 0.14 |
| 111 | T67N | 67 | T | N | 0.18 | 0.01 |
| 112 | N46S | 46 | N | S | 0.18 | 0.08 |
| 113 | E24M | 24 | E | M | 0.18 | 0.21 |
| 114 | K4S | 4 | K | S | 0.18 | 0.13 |
| 115 | A68Q | 68 | A | Q | 0.18 | 0.14 |
| 116 | K30T | 30 | K | T | 0.18 | 0.37 |
| 117 | T38R | 38 | T | R | 0.17 | 0.18 |
| 118 | W18F | 18 | W | F | 0.17 | 0.29 |
| 119 | K3N | 3 | K | N | 0.17 | 0.18 |
| 120 | N37Q | 37 | N | Q | 0.17 | 0.17 |
| 121 | L52W | 52 | L | W | 0.17 | 0.16 |
| 122 | L35A | 35 | L | A | 0.16 | 0.30 |
| 123 | S42M | 42 | S | M | 0.16 | 0.28 |
| 124 | K44Y | 44 | K | Y | 0.16 | 0.29 |
| 125 | L35K | 35 | L | K | 0.16 | 0.14 |
| 126 | A68G | 68 | A | G | 0.16 | 0.24 |
| 127 | T67E | 67 | T | E | 0.16 | 0.17 |
| 128 | K33P | 33 | K | P | 0.16 | 0.18 |
| 129 | K30I | 30 | K | I | 0.15 | 0.16 |
| 130 | T22M | 22 | T | M | 0.15 | 0.05 |
| 131 | K26G | 26 | K | G | 0.15 | 0.18 |
| 132 | L51A | 51 | L | A | 0.15 | 0.21 |
| 133 | G36V | 36 | G | V | 0.15 | 0.34 |
| 134 | D39N | 39 | D | N | 0.15 | 0.11 |
| 135 | I43W | 43 | I | W | 0.15 | 0.01 |
| 136 | T38E | 38 | T | E | 0.15 | 0.16 |
| 137 | T22G | 22 | T | G | 0.15 | 0.08 |
| 138 | E60S | 60 | E | S | 0.14 | 0.08 |
| 139 | M1T | 1 | M | T | 0.14 | 0.23 |
| 140 | T38M | 38 | T | M | 0.14 | 0.12 |
| 141 | A19S | 19 | A | S | 0.14 | 0.34 |
| 142 | K26T | 26 | K | T | 0.14 | 0.23 |
| 143 | K65L | 65 | K | L | 0.13 | 0.05 |
| 144 | E24P | 24 | E | P | 0.13 | 0.23 |
| 145 | K45N | 45 | K | N | 0.13 | 0.02 |
| 146 | T38W | 38 | T | W | 0.13 | 0.07 |
| 147 | K3A | 3 | K | A | 0.13 | 0.26 |
| 148 | I48F | 48 | I | F | 0.13 | 0.28 |
| 149 | I11L | 11 | I | L | 0.13 | 0.08 |
| 150 | M1I | 11 | M | I | 0.13 | 0.13 |
| 151 | E57N | 57 | E | N | 0.13 | 0.52 |
| 152 | I43V | 43 | I | V | 0.12 | 0.16 |
| 153 | T22A | 22 | T | A | 0.12 | 0.10 |
| 154 | V16M | 16 | V | M | 0.12 | 0.20 |
| 155 | K26E | 26 | K | E | 0.12 | 0.06 |
| 156 | S55C | 55 | S | C | 0.12 | 0.16 |
| 157 | N37W | 37 | N | W | 0.11 | 0.33 |
| 158 | K44C | 44 | K | C | 0.11 | 0.09 |
| 159 | T38K | 38 | T | K | 0.11 | 0.19 |
| 160 | L35M | 35 | L | M | 0.11 | 0.17 |
| 161 | K31S | 31 | K | S | 0.11 | 0.35 |
| 162 | N37S | 37 | N | S | 0.11 | 0.05 |
| 163 | K44P | 44 | K | P | 0.11 | 0.05 |
| 164 | K4Q | 4 | K | Q | 0.11 | 0.15 |
| 165 | G36D | 36 | G | D | 0.10 | 0.27 |
| 166 | K3C | 3 | K | C | 0.10 | 0.21 |
| 167 | K3M | 3 | K | M | 0.10 | 0.22 |
| 168 | T22E | 22 | T | E | 0.10 | 0.22 |
| 169 | S42F | 42 | S | F | 0.10 | 0.26 |
| 170 | S29L | 29 | S | L | 0.10 | 0.09 |
| 171 | L9S | 9 | L | S | 0.10 | 0.17 |
| 172 | N37D | 37 | N | D | 0.10 | 0.16 |
| 173 | A19C | 19 | A | C | 0.10 | 0.10 |
| 174 | K4M | 4 | K | M | 0.09 | 0.08 |
| 175 | Y72A | 72 | Y | A | 0.09 | 0.26 |
| 176 | I21Ter | 21 | I | r | 0.09 | 0.18 |
| 177 | N37H | 37 | N | H | 0.09 | 0.27 |
| 178 | L35S | 35 | L | S | 0.09 | 0.15 |
| 179 | K45H | 45 | K | H | 0.08 | 0.09 |
| 180 | V16L | 16 | V | L | 0.08 | 0.03 |
| 181 | N46I | 46 | N | I | 0.08 | 0.11 |
| 182 | I43S | 43 | 1 | S | 0.08 | 0.19 |
| 183 | V34M | 34 | V | M | 0.08 | 0.32 |
| 184 | I43G | 43 | I | G | 0.08 | 0.34 |
| 185 | M1V | 1 | M | V | 0.08 | 0.16 |
| 186 | T38F | 38 | T | F | 0.08 | 0.19 |
| 187 | K45R | 45 | K | R | 0.08 | 0.15 |
| 188 | I11V | 11 | I | V | 0.08 | 0.08 |

TABLE 2-continued

Point mutations enriched over WT SpCas9 (SEQ ID NO: 1). Shown in natural log, phenotype enrichment scores demonstrate point mutations of improving Cas9 activity.

| Number | Mutation | Position | Wild-Type Residue | Mutation Residue | Average | Standard Deviation |
|---|---|---|---|---|---|---|
| 189 | A68V | 68 | A | V | 0.08 | 0.09 |
| 190 | S29T | 29 | S | T | 0.07 | 0.20 |
| 191 | R40G | 40 | R | G | 0.07 | 0.14 |
| 192 | I43R | 43 | I | R | 0.07 | 0.15 |
| 193 | S42L | 42 | S | L | 0.07 | 0.12 |
| 194 | I43T | 43 | I | T | 0.07 | 0.10 |
| 195 | T22Y | 22 | T | Y | 0.07 | 0.29 |
| 196 | D39L | 39 | D | L | 0.07 | 0.10 |
| 197 | R40C | 40 | R | C | 0.07 | 0.09 |
| 198 | T38L | 38 | T | L | 0.07 | 0.03 |
| 199 | K26L | 26 | K | L | 0.07 | 0.49 |
| 200 | E24L | 24 | E | L | 0.06 | 0.10 |
| 201 | K33V | 33 | K | V | 0.06 | 0.33 |
| 202 | K44V | 44 | K | V | 0.06 | 0.05 |
| 203 | A68T | 68 | A | T | 0.06 | 0.06 |
| 204 | T38V | 38 | T | V | 0.06 | 0.15 |
| 205 | K3I | 3 | K | I | 0.06 | 0.35 |
| 206 | L64R | 64 | L | R | 0.06 | 0.08 |
| 207 | N37R | 37 | N | R | 0.06 | 0.12 |
| 208 | N37G | 37 | N | G | 0.06 | 0.29 |
| 209 | T38Y | 38 | T | Y | 0.06 | 0.23 |
| 210 | D39F | 39 | D | F | 0.06 | 0.08 |
| 211 | K44L | 44 | K | L | 0.05 | 0.07 |
| 212 | K26W | 26 | K | W | 0.05 | 0.04 |
| 213 | I43L | 43 | I | L | 0.05 | 0.05 |
| 214 | S42K | 42 | S | K | 0.05 | 0.08 |
| 215 | L35Q | 35 | L | Q | 0.05 | 0.12 |
| 216 | T67R | 67 | T | R | 0.05 | 0.17 |
| 217 | E57K | 57 | E | K | 0.05 | 0.03 |
| 218 | D39A | 39 | D | A | 0.04 | 0.20 |
| 219 | T62W | 62 | T | W | 0.04 | 0.19 |
| 220 | V34A | 34 | V | A | 0.04 | 0.13 |
| 221 | A61R | 61 | A | R | 0.04 | 0.20 |
| 222 | K26M | 26 | K | M | 0.04 | 0.23 |
| 223 | S29G | 29 | S | G | 0.04 | 0.23 |
| 224 | A68F | 68 | A | F | 0.04 | 0.07 |
| 225 | T22Q | 22 | T | Q | 0.04 | 0.14 |
| 226 | A68H | 68 | A | H | 0.04 | 0.32 |
| 227 | I43F | 43 | I | F | 0.04 | 0.16 |
| 228 | P28L | 28 | P | L | 0.03 | 0.18 |
| 229 | R40S | 40 | R | S | 0.03 | 0.21 |
| 230 | K3L | 3 | K | L | 0.03 | 0.47 |
| 231 | V16A | 16 | V | A | 0.03 | 0.21 |
| 232 | T38H | 38 | T | H | 0.03 | 0.20 |
| 233 | G36S | 36 | G | S | 0.03 | 0.19 |
| 234 | T22H | 22 | T | H | 0.03 | 0.11 |
| 235 | K45E | 45 | K | E | 0.03 | 0.18 |
| 236 | I43Q | 43 | I | Q | 0.03 | 0.32 |
| 237 | N37P | 37 | N | P | 0.03 | 0.05 |
| 238 | W18Y | 18 | W | Y | 0.03 | 0.23 |
| 239 | S42P | 42 | S | P | 0.03 | 0.11 |
| 240 | V34E | 34 | V | E | 0.02 | 0.11 |
| 241 | S42Y | 42 | S | Y | 0.02 | 0.12 |
| 242 | L47W | 47 | L | W | 0.02 | 0.10 |
| 243 | A68M | 68 | A | M | 0.02 | 0.27 |
| 244 | A68C | 68 | A | C | 0.02 | 0.09 |
| 245 | I43A | 43 | I | A | 0.02 | 0.11 |
| 246 | V20I | 20 | V | I | 0.02 | 0.19 |
| 247 | E57H | 57 | E | H | 0.02 | 0.45 |
| 248 | K26R | 26 | K | R | 0.02 | 0.23 |
| 249 | K65H | 65 | K | H | 0.02 | 0.11 |
| 250 | K44I | 44 | K | I | 0.02 | 0.02 |
| 251 | T22C | 22 | T | C | 0.02 | 0.15 |
| 252 | T73A | 73 | T | A | 0.02 | 0.13 |
| 253 | S42W | 42 | S | W | 0.02 | 0.21 |
| 254 | Y25W | 25 | Y | W | 0.02 | 0.05 |
| 255 | K45T | 45 | K | T | 0.01 | 0.08 |
| 256 | K65Q | 65 | K | Q | 0.01 | 0.16 |
| 257 | M1L | 1 | M | L | 0.01 | 0.06 |
| 258 | S42E | 42 | S | E | 0.01 | 0.06 |
| 259 | L64K | 64 | L | K | 0.01 | 0.12 |
| 260 | I43K | 43 | I | K | 0.01 | 0.09 |
| 261 | K26S | 26 | K | S | 0.01 | 0.31 |
| 262 | K44F | 44 | K | F | 0.01 | 0.19 |
| 263 | K4N | 4 | K | N | 0.01 | 0.32 |
| 264 | K4T | 4 | K | T | 0.01 | 0.12 |
| 265 | F32L | 32 | F | L | 0.01 | 0.10 |
| 266 | I11G | 11 | I | G | 0.01 | 0.08 |

We next evaluated the performance of novel Cas9 point mutations in the context of genome editing of human cells. We selectively introduced 9 point mutations identified in the E. coli screen on Hifi-Cas9 (R691A) (polypeptide sequence: SEQ ID NO: 4; codon-optimized nucleic acid sequences: SEQ ID NO: 5 and 6). Each mutant protein was expressed in E. coli and purified through sequential chromatography. The on-target editing efficiency of each mutant was evaluated over 3 target sites (Table 3).

TABLE 3

Target sites used to assess on- and off-target activities of SpCas9 mutants

| Target site | Protospacer (5'-3') | PAM |
|---|---|---|
| EMX1 | GAGTCCGAGCAGAAGAAGAA | GGG |
| HPRT 38358 | ATTTCACATAAAACTCTTTT | AGG |
| HPRT 38231 | TTTTGTAATTAACAGCTTGC | TGG |
| EMX1 off-target | GAGTTAGAGCAGAAGAAGAA | AGG |

Figure 3A:
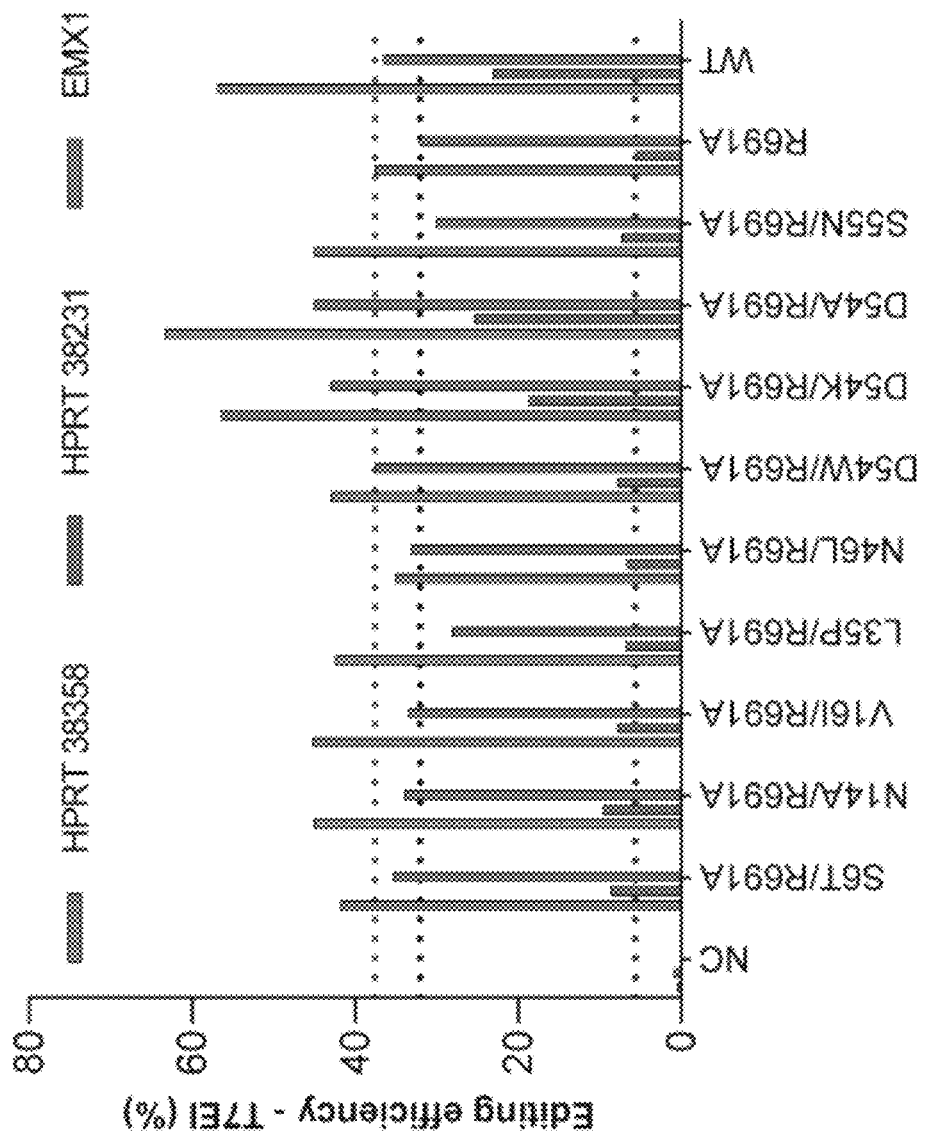
FIG. 3A depicts exemplary SpCas9 mutants with enhanced on-target editing efficiency in human cells. Putative mutations with beneficial effect in *E. coli* activity assay was introduced in the background of Hifi-Cas9 (R691A). Mutant proteins were purified, and evaluated in HEK293 cells by editing three target sites. On-target editing efficiency of novel Cas9 mutants. The dot lines highlight the editing efficiency of reference protein (R691A) at each target.
Figure 3B:
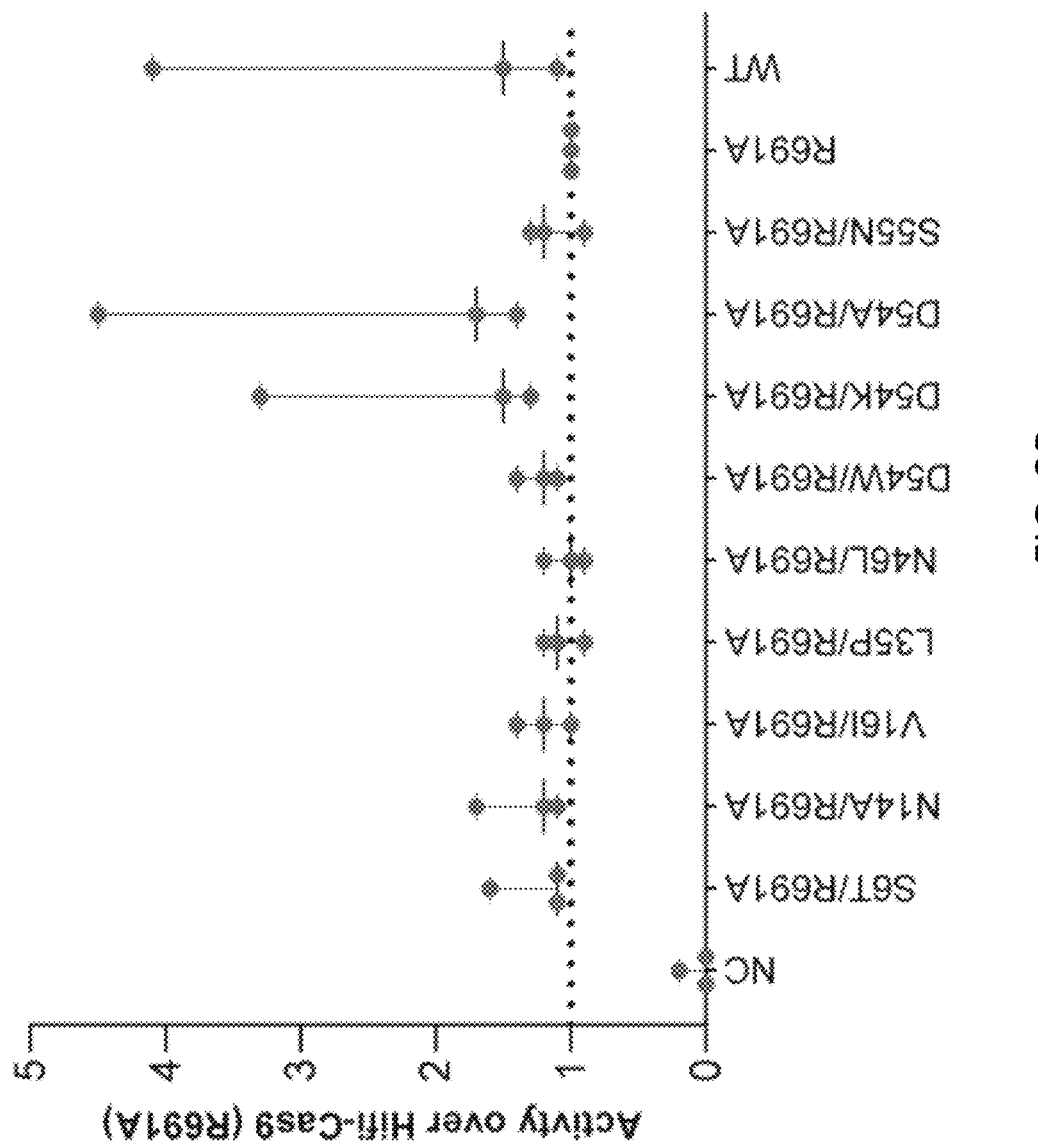
FIG. 3B depicts normalized editing efficiency of each mutant against reference protein (R691A). Of note, D54A/K significantly elevated the on-target activity of R691A, even surpassing WT-SpCas9.
Figure 3C:
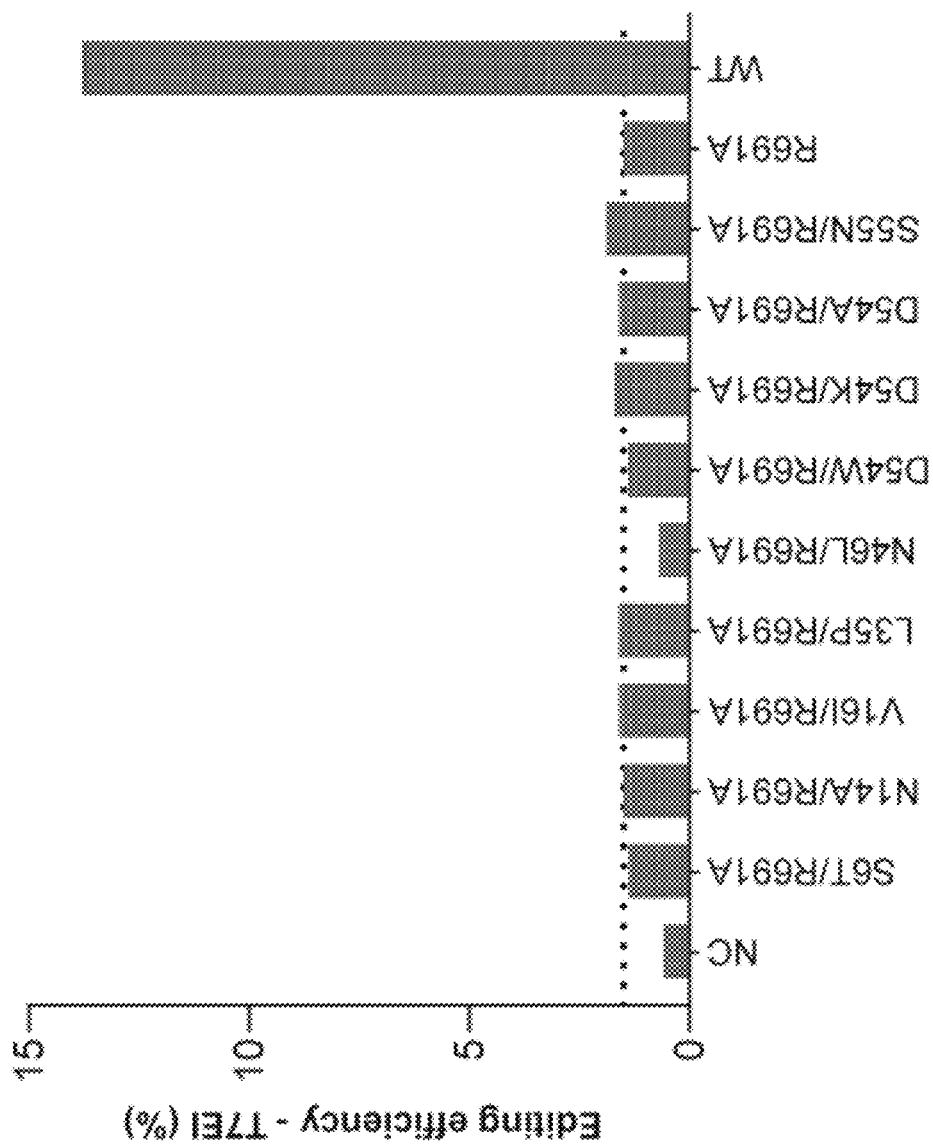
FIG. 3C depicts off-target editing of novel Cas9 mutants at EMX1 off-target site. Only WT-SpCas9 displayed any measurable off-target effect. All novel Cas9 mutants remained highly specific.

Satisfyingly, these point mutations elevated the on-target potency of Hifi-Cas9 (FIG. 3A, B), thus validating our previous results generated in E. coli. Of note, D54A resulted in the most significant boost of on-target potency, particularly at the low-activity site (HPRT38231) that is poorly edited by Hifi-Cas9. The activity of this novel variant (D54A/R691A) is even higher than WT-SpCas9 (FIG. 3A, B). We further studied the off-target editing level of novel Cas9 variants at EMX1 off-target site 1 (Table 3). Surprisingly, none of the mutant significantly increased the off-target effect, suggesting these novel mutants are compatible with Hifi-Cas9 (R691A), and affect the overall Cas9 protein activity at on- and off-target sites through different mechanism than R691A. In conclusion, our data demonstrated that the novel point mutations uncovered by our bacterial screen can enhance the on-target performance of Hifi-Cas9 while maintaining its excellent targeting specificity, which could serve as a direct replacement of WT-SpCas9 for human genome engineering.

Preferred single mutant Cas9 proteins include substitution mutations in the WT-Cas9 introduced at one of the positions identified in Table 2. Additional substitution mutations can be included in the amino acid backgrounds of the single mutant Cas9 protein amino acid sequences, provided that the resultant mutant Cas9 protein is active as a CRISPR/Cas endonuclease system, wherein the resultant CRISPR/Cas endonuclease system displays increased on-target editing activity relative to a wild-type CRISPR/Cas endonuclease system.

Preferred double mutant Cas9 proteins include mutations in the WT-Cas9 introduced into R691 in combination with one of the mutations presented in Table 2. Highly preferred double mutant Cas9 proteins include mutations in the WT-Cas9 introduced at having R691A in combination with one of the mutations presented in Table 2. Additional substitution mutations can be included in the amino acid backgrounds of the double mutant Cas9 protein amino acid sequences, provided that the resultant mutant Cas9 protein is active as a CRISPR/Cas endonuclease system, wherein the resultant CRISPR/Cas endonuclease system displays increased on-target editing activity relative to a wild-type CRISPR/Cas endonuclease system. Exemplary mutations presented in Table 2 may be combined, for example at other positions, such as those disclosed in U.S. patent application Ser. Nos. 15/729,491 and 15/964,041, filed Oct. 10, 2017 and Apr. 26, 2018, the contents of which are incorporated by reference herein.

In a second aspect, an isolated ribonucleoprotein complex is provided. The RNP includes a mutant Cas9 protein and a gRNA complex. In one respect, the gRNA includes a crRNA and a tracrRNA in stoichiometric (1:1) ratio. In a second respect the crRNA includes an Alt-R® crRNA (Integrated DNA Technologies, Inc. (Coralville, IA (US)) directed against a specific editing target site for a given locus and the tracrRNA includes Alt-R® tracrRNA (Integrated DNA Technologies, Inc. (Coralville, IA (US)). In another respect the gRNA includes a sgRNA. Preferred mutant Cas9 proteins include those as described above.

In a third aspect, an isolated nucleic acid encoding a mutant Cas9 protein is provided. Preferred isolated nucleic acids encode mutant Cas9 proteins as described above. Exemplary isolated nucleic acids encoding mutant Cas9 proteins can be readily generated from a nucleic acid encoding the wild-type Cas9 protein using recombinant DNA procedures or chemical synthesis methods. Preferred nucleic acids for this purpose include those optimized for expression of the Cas9 proteins in bacteria (e.g., *E. coli*) or mammalian (e.g., human) cells. Exemplary codon-optimized nucleic acids for expressing WT-Cas9 (SEQ ID NO: 1) in *E. coli* and human cells include SEQ ID NO: 1 and 2, respectively. Exemplary codon-optimized nucleic acids for expressing mutant Cas9 protein (e.g., R691A mutant Cas9 protein; SEQ ID NO: 7) in *E. coli* and human cells include SEQ ID NO: 3 and 4, respectively. Moreover, the present invention contemplates fusion proteins of WT-Cas9 and mutant Cas9, wherein the coding sequences of WT-Cas9 and mutant Cas9 are fused to amino acid sequences encoding for nuclear localization ("NLS") of the fusion protein in eukaryotic cells or amino acid sequences to facilitate purification of the proteins. Exemplary fusion proteins that include either the WT-Cas9 amino acid sequence or a mutant Cas9 amino acid sequence (e.g., R691A mutant Cas9 protein).

In one respect, the isolated nucleic acid includes mRNA encoding one of the aforementioned mutant Cas9 proteins. In a second respect, the isolated nucleic acid includes DNA encoding a gene for one of the aforementioned mutant Cas9 proteins. A preferred DNA includes a vector that encodes a gene encoding for a mutant Cas9 protein. Such delivery methods include plasmid and various viral delivery vectors as are well known to those with skill in the art. The mutant Cas9 protein can also be stably transformed into cells using suitable expression vectors to produce a cell line that constitutively or inducibly expresses the mutant Cas9. The aforementioned methods can also be applied to embryos to product progeny animals that constitutively or inducibly expresses the mutant Cas9.

In a fourth aspect, a CRISPR/Cas endonuclease system is provided. The CRISPR/Cas endonuclease system includes a mutant Cas9 protein. Preferred mutant Cas9 proteins include those as described above. In one respect, the CRISPR/Cas endonuclease system is encoded by a DNA expression vector. In one embodiment, the DNA expression vector is a plasmid-borne vector. In a second embodiment, the DNA expression vector is selected from a bacterial expression vector and a eukaryotic expression vector. In third respect, the CRISPR/Cas endonuclease system comprises a ribonucleoprotein complex comprising a mutant Cas9 protein and a gRNA complex. In one respect, the gRNA includes a crRNA and a tracrRNA in stoichiometric (1:1) ratio. In a second respect the crRNA includes an ALT-R® crRNA (Integrated DNA Technologies, Inc. (Coralville, IA (US)) directed against a specific editing target site for a given locus and the tracrRNA includes ALT-R® tracrRNA (Integrated DNA Technologies, Inc. (Coralville, IA (US)). In another respect the gRNA includes a sgRNA.

In a fifth aspect, a method of performing gene editing having increased on-target editing activity is provided. The method includes the step of contacting a candidate editing target site locus with an active CRISPR/Cas endonuclease system having a mutant Cas9 protein. In one respect, the method includes single mutant Cas9 proteins having mutations in the WT-Cas9 of SEQ ID NO: 1 introduced at one of the positions presented in Table 2. Additional substitution mutations can be included in the amino acid backgrounds of the single mutant Cas9 protein amino acid sequences, provided that the resultant mutant Cas9 protein is active as a CRISPR/Cas endonuclease system in the method, wherein the resultant CRISPR/Cas endonuclease system displays increased on-target editing activity relative to a wild-type CRISPR/Cas endonuclease system.

In another respect, the method includes Cas9 protein variants having mutations in the WT-Cas9 of SEQ ID NO: 1 introduced at positions R691 in combination with one of the mutations presented in Table 2. Additional substitution mutations can be included in the amino acid backgrounds of the double mutant Cas9 protein amino acid sequences, provided that the resultant mutant Cas9 protein is active as a CRISPR/Cas endonuclease system in the method, wherein the resultant CRISPR/Cas endonuclease system displays increased on-target editing activity relative to a wild-type CRISPR/Cas endonuclease system.

The applications of Cas9-based tools are many and varied. They include, but are not limited to: plant gene editing, yeast gene editing, mammalian gene editing, editing of cells in the organs of live animals, editing of embryos, rapid generation of knockout/knock-in animal lines, generating an animal model of disease state, correcting a disease state, inserting a reporter gene, and whole genome functional screening.

Example 1

DNA and Amino Acid Sequences of Select Wild Type and Mutant Cas9 Proteins.

The list below shows different wild type (WT) and mutant Cas9 nucleases described in the present invention. It will be appreciated by one with skill in the art that many different DNA sequences can encode/express the same amino acid (AA) sequence since in many cases more than one codon can encode for the same amino acid. The DNA sequences shown below only serve as example and other DNA sequences that encode the same protein (e.g., same amino acid sequence)

are contemplated. It is further appreciated that additional features, elements or tags may be added to said sequences, such as NLS domains and the like. Examples are shown for WT Cas9 and mutant R691A Cas9 showing amino acid and DNA sequences for those proteins as Cas9 alone and Cas9 fused to both C-terminal and N-terminal SV40 NLS domains and a HIS-tag. For other Cas9 mutants, only the amino-acid sequences are provided, but it is contemplated that similar additions of NLS and His-tag domains may be added to facilitate use in producing recombinant proteins for use in mammalian cells. Mutations that differ from the WT sequence are identified using bold font with underline.

```
WT SpyCas9 AA sequence.
                                                              SEQ ID NO: 1
MDKKYSIGLDIGTNSVGWAVITDEYKVPSKKFKVLGNTDRHSIKKNLIGALLFDSGETAEATRLKRTARRRYTR

RKNRICYLQEIFSNEMAKVDDSFFHRLEESFLVEEDKKHERHPIFGNIVDEVAYHEKYPTIYHLRKKLVDSTDK

ADLRLIYLALAHMIKFRGHFLIEGDLNPDNSDVDKLFIQLVQTYNQLFEENPINASGVDAKAILSARLSKSRRL

ENLIAQLPGEKKNGLFGNLIALSLGLTPNFKSNFDLAEDAKLQLSKDTYDDDLDNLLAQIGDQYADLFLAAKNL

SDAILLSDILRVNTEITKAPLSASMIKRYDEHHQDLTLLKALVRQQLPEKYKEIFFDQSKNGYAGYIDGGASQE

EFYKFIKPILEKMDGTEELLVKLNREDLLRKQRTFDNGSIPHQIHLGELHAILRRQEDFYPFLKDNREKIEKIL

TFRIPYYVGPLARGNSRFAWMTRKSEETITPWNFEEVVDKGASAQSFIERMTNFDKNLPNEKVLPKHSLLYEYF

TVYNELTKVKYVTEGMRKPAFLSGEQKKAIVDLLFKTNRKVTVKQLKEDYFKKIECFDSVEISGVEDRFNASLG

TYHDLLKIIKDKDFLDNEENEDILEDIVLTLTLFEDREMIEERLKTYAHLFDDKVMKQLKRRRYTGWGRLSRKL

INGIRDKQSGKTILDFLKSDGFANRNFMQLIHDDSLTFKEDIQKAQVSGQGDSLHEHIANLAGSPAIKKGILQT

VKVVDELVKVMGRHKPENIVIEMARENQTTQKGQKNSRERMKRIEEGIKELGSQILKEHPVENTQLQNEKLYLY

YLQNGRDMYVDQELDINRLSDYDVDHIVPQSFLKDDSIDNKVLTRSDKNRGKSDNVPSEEVVKKMKNYWRQLLN

AKLITQRKFDNLTKAERGGLSELDKAGFIKRQLVETRQITKHVAQILDSRMNTKYDENDKLIREVKVITLKSKL

VSDFRKDFQFYKVREINNYHHAHDAYLNAVVGTALIKKYPKLESEFVYGDYKVYDVRKMIAKSEQEIGKATAKY

FFYSNIMNFFKTEITLANGEIRKRPLIETNGETGEIVWDKGRDFATVRKVLSMPQVNIVKKTEVQTGGFSKESI

LPKRNSDKLIARKKDWDPKKYGGFDSPTVAYSVLVVAKVEKGKSKKLKSVKELLGITIMERSSFEKNPIDFLEA

KGYKEVKKDLIIKLPKYSLFELENGRKRMLASAGELQKGNELALPSKYVNFLYLASHYEKLKGSPEDNEQKQLF

VEQHKHYLDEIIEQISEFSKRVILADANLDKVLSAYNKHRDKPIREQAENIIHLFTLTNLGAPAAFKYFDTTID

RKRYTSTKEVLDATLIHQSITGLYETRIDLSQLGGD

WT SpyCas9 DNA sequence, codon optimized for expression in E. coli.
                                                              SEQ ID NO: 2
ATGGGCAGCAGCGCCCCAAAGAAGAAGCGGAAGGTCGGTATCCACGGAGTCCCAGCAGCCATGGACAAAAAGTA

CTCTATTGGCCTGGATATCGGGACCAACAGCGTCGGGTGGGCTGTTATCACCGACGAGTATAAAGTACCTTCGA

AAAAGTTCAAAGTGCTGGGCAACACCGATCGCCATTCAATCAAAAAGAACTTGATTGGTGCGCTGTTGTTTGAC

TCCGGGGAAACCGCCGAGGCGACTCGCCTTAAACGTACAGCACGTCGCCGGTACACTCGGCGTAAGAATCGCAT

TTGCTATTTGCAGGAAATCTTTAGCAACGAGATGGCAAAGTCGATGACTCGTTTTTCCACCGCCTCGAGGAAA

GCTTTCTGGTGGAGGAAGACAAAAAGCATGAGCGTCACCCGATCTTCGGCAACATTGTCGATGAAGTAGCGTAT

CATGAAAAATACCCAACCATTTACCACTTACGCAAAAAGCTGGTGGACAGCACTGACAAAGCTGATTTGCGCCT

TATCTATTTAGCCCTGGCACATATGATTAAGTTTCGTGGTCACTTCCTGATCGAAGGAGACTTAAATCCCGACA

ACAGTGATGTTGATAAATTGTTTATTCAGCTTGTCCAAACTTACAATCAACTGTTCGAGGAAAACCCGATCAAT

GCCTCCGGTGTGGATGCAAAAGCCATTTTAAGTGCACGCCTTAGCAAGTCCCGTCGCTTAGAAAACCTTATCGC

GCAGCTGCCCGGCGAGAAAAAGAATGGTTTGTTTGGGAACCTTATTGCCTTGAGCTTAGGCCTCACCCCGAATT

TCAAAAGTAATTTCGATCTTGCAGAAGACGCCAAATTACAACTGTCGAAGGATACTTATGATGACGATCTCGAT

AATCTGTTAGCGCAGATTGGTGACCAATACGCCGATCTTTTTCTGGCGGCTAAAAATCTGAGCGACGCCATCTT

GCTTTCGGATATTCTCCGCGTTAACACCGAAATCACGAAAGCGCCTCTTAGTGCCAGCATGATTAAACGTTATG

ATGAACACCACCAGGACCTGACCTTACTCAAAGCGTTGGTTCGCCAGCAACTGCCAGAGAAGTACAAAGAAATC

TTCTTTGATCAGTCAAAGAATGGTTATGCCGGCTATATTGACGGGGGTGCAAGCCAAGAGGAATTCTACAAATT
```

-continued

```
TATCAAGCCTATTCTGGAGAAAATGGATGGCACCGAAGAGTTATTGGTGAAGCTTAACCGTGAAGACCTCCTGC

GGAAACAGCGCACATTCGATAATGGTTCGATCCCACACCAAATCCATTTGGGGGAGTTACACGCTATTTTGCGT

CGCCAGGAAGACTTTTACCCTTTCCTGAAGGATAACCGGGAGAAAATTGAGAAGATCCTTACCTTTCGTATTCC

GTATTACGTAGGCCCCTTAGCACGGGGTAATAGCCGTTTCGCGTGGATGACACGGAAGTCGGAAGAGACGATCA

CCCCGTGGAACTTCGAAGAGGTAGTCGACAAGGGCGCATCAGCGCAGTCTTTTATTGAACGTATGACGAATTTC

GATAAAAACTTGCCCAATGAGAAGGTGCTTCCGAAACATTCCTTGTTATATGAATATTTTACAGTTTACAACGA

GCTGACCAAGGTTAAATACGTGACGGAAGGAATGCGCAAGCCCGCTTTTCTTAGCGGTGAGCAAAAAAGGCGA

TCGTCGACCTGTTATTCAAAACGAATCGTAAGGTGACTGTAAAGCAACTCAAAGAAGATTACTTCAAAAAGATT

GAGTGCTTCGACAGCGTCGAAATCTCTGGGGTAGAGGATCGGTTTAACGCAAGTTTAGGTACCTACCATGACCT

GCTTAAAATCATTAAGGATAAAGACTTCTTAGATAATGAAGAGAACGAAGATATTCTCGAGGACATCGTCTTGA

CGTTAACCTTATTTGAGGATCGTGAAATGATTGAGGAACGCCTCAAAACTTATGCCCACCTGTTCGACGATAAG

GTGATGAAGCAGCTGAAACGTCGGCGCTACACAGGATGGGGCCGCTTGAGTCGCAAACTTATTAACGGAATCCG

TGACAAGCAATCCGGCAAAACGATTCTGGATTTCTTGAAGTCGGACGGATTTGCTAATCGCAACTTCATGCAGT

TGATCCATGATGACTCCCTGACTTTTAAAGAGGATATTCAAAAGGCGCAGGTTAGTGGTCAAGGCGACAGCTTA

CACGAACACATCGCAAATTTGGCTGGTTCGCCGGCCATTAAAAAGGGGATCCTCCAGACCGTGAAAGTTGTAGA

TGAGCTTGTTAAGGTCATGGGTCGTCATAAGCCCGAAAACATCGTGATTGAAATGGCGCGGGAGAATCAAACGA

CCCAGAAAGGACAAAAGAATAGCCGTGAACGGATGAAGCGGATCGAGGAAGGCATTAAAGAGCTGGGGTCTCAA

ATCTTGAAGGAACACCCTGTGGAGAACACTCAGCTCCAAAATGAAAAACTTTACCTGTACTATTTGCAGAACGG

ACGCGATATGTACGTGGACCAAGAGTTGGATATTAATCGGCTGAGTGACTACGACGTTGATCATATCGTCCCGC

AGAGCTTCCTCAAAGACGATTCTATTGACAATAAGGTACTGACGCGCTCTGATAAAAACCGTGGTAAGTCGGAC

AACGTGCCCTCCGAAGAGGTTGTGAAAAAGATGAAAAATTATTGGCGCCAGCTTTTAAACGCGAAGCTGATCAC

ACAACGTAAATTCGATAATTTGACCAAGGCTGAACGGGGTGGCCTGAGCGAGTTAGATAAGGCAGGATTTATTA

AACGCCAGTTAGTGGAGACTCGTCAAATCACCAAACATGTCGCGCAGATTTTGGACAGCCGGATGAACACCAAG

TAGGATGAAAATGACAAACTGATCCGTGAGGTGAAAGTCATTACTCTGAAGTCCAAATTAGTTAGTGATTTCCG

GAAGGACTTTCAATTCTACAAAGTCCGTGAAATTAATAACTATCATCACGCACATGACGCGTACCTGAATGCAG

TGGTTGGGACCGCCCTTATCAAGAAATATCCTAAGCTGGAGTCGGAGTTTGTCTATGGCGACTATAAGGTATAC

GATGTTCGCAAAATGATTGCGAAATCTGAGCAGGAGATCGGTAAGGCAACCGCAAAATATTTCTTTTACTCAAA

CATTATGAATTTCTTTAAGACAGAAATCACTCTGGCCAACGGGGAGATTCGCAAACGTCCGTTGATCGAAACAA

ACGGCGAGACTGGCGAAATTGTTTGGGACAAAGGGCGTGATTTCGCGACGGTGCGCAAGGTACTGAGCATGCCT

CAAGTCAATATTGTTAAGAAAACCGAAGTGCAGACGGGCGGGTTTTCCAAGGAAAGCATCTTACCCAAACGTAA

TTCAGATAAACTTATTGCACGCAAAAAGGACTGGGATCCGAAAAAGTATGGAGGCTTCGACAGTCCAACCGTAG

CCTACTCTGTTCTCGTTGTAGCGAAAGTAGAAAAGGGTAAATCCAAGAAACTGAAATCTGTCAAGGAGTTGCTT

GGAATCACCATTATGGAGCGTAGCTCCTTCGAGAAGAACCCGATTGACTTTCTGGAAGCCAAAGGATATAAAGA

GGTCAAGAAAGATCTTATCATTAAGCTGCCTAAGTATTCACTCTTCGAGCTGGAAAATGGTCGTAAACGCATGC

TCGCTTCTGCCGGCGAGTTGCAGAAGGGCAATGAATTAGCACTTCCATCAAAGTACGTTAACTTCCTGTATTTG

GCCAGCCATTACGAGAAACTGAAGGGGTCTCCAGAGGACAACGAACAGAAACAATTATTTGTAGAGCAGCACAA

GCATTATCTTGATGAAATCATTGAGCAAATTTCCGAATTCAGTAAACGCGTAATCCTGGCCGATGCAAACCTCG

ACAAGGTGCTGAGCGCTTACAATAAGCATCGCGACAAACCTATCCGTGAGCAGGCTGAAAATATCATTCACCTG

TTCACATTAACGAACCTGGGCGCTCCGGCCGCTTTTAAATATTTCGACACGACAATCGACCGTAAGCGCTATAC

CAGTACGAAAGAAGTGTTGGATGCGACCCCTTATTCACCAGTCAATTACAGGATTATATGAGACCCGTATCGACC
```

-continued

TTAGCCAATTAGGTGGGGATGCGGCCCCGAAGAAAAAACGCAAAGTGGATCCGAAGAAAAAACGCAAAGTGGCG

GCCGCACTCGAGCACCACCACCACCACCACTGA

WT SpyCas9 DNA sequence, codon optimized for expression in *H. sapiens*.
SEQ ID NO: 3

ATGGGCAAGCCCATCCCTAACCCCCTGTTGGGGCTGGACAGCACCGCTCCCAAAAAGAAAAGGAAGGTGGGCAT

TCACGGCGTGCCTGCGGCCGACAAAAAGTACAGCATCGGCCTTGATATCGGCACCAATAGCGTGGGCTGGGCCG

TTATCACAGACGAATACAAGGTACCCAGCAAGAAGTTCAAGGTGCTGGGGAATACAGACAGGCACTCTATCAAG

AAAAACCTTATCGGGGCTCTGCTGTTTGACTCAGGCGAGACCGCCGAGGCCACCAGGTTGAAGAGGACCGCAAG

GCGAAGGTACACCCGGAGGAAGAACAGGATCTGCTATCTGCAGGAGATCTTCAGCAACGAGATGGCCAAGGTGG

ACGACAGCTTCTTCCACAGGCTGGAGGAGAGCTTCCTTGTCGAGGAGGATAAGAAGCACGAACGACACCCCATC

TTCGGCAACATAGTCGACGAGGTCGCTTATCACGAGAAGTACCCCACCATCTACCACCTGCGAAAGAAATTGGT

GGATAGCACCGATAAAGCCGACTTGCGACTTATCTACTTGGCTCTGGCGCACATGATTAAGTTCAGGGGCCACT

TCCTGATCGAGGGCGACCTTAACCCCGACAACAGTGACGTAGACAAATTGTTCATCCAGCTTGTACAGACCTAT

AACCAGCTGTTCGAGGAAAACCCTATTAACGCCAGCGGGGTGGATGCGAAGGCCATACTTAGCGCCAGGCTGAG

CAAAAGCAGGCGCTTGGAGAACCTGATAGCCCAGCTGCCCGGTGAAAAGAAGAACGGCCTCTTCGGTAATCTGA

TTGCCCTGAGCCTGGGCCTGACCCCCAACTTCAAGAGCAACTTCGACCTGGCAGAAGATGCCAAGCTGCAGTTG

AGTAAGGACACCTATGACGACGACTTGGACAATCTGCTCGCCCAAATCGGCGACCAGTACGCTGACCTGTTCCT

CGCCGCCAAGAACCTTTCTGACGCAATCCTGCTTAGCGATATCCTTAGGGTGAACACAGAGATCACCAAGGCCC

CCCTGAGCGCCAGCATGATCAAGAGGTACGACGAGCACCATCAGGACCTGACCCTTCTGAAGGCCCTGGTGAGG

CAGCAACTGCCCGAGAAGTACAAGGAGATCTTTTTCGACCAGAGCAAGAACGGCTACGCCGGCTACATCGACGG

CGGAGCCAGCCAAGAGGAGTTCTACAAGTTCATCAAGCCCATCCTGGAGAAGATGGATGGCACCGAGGAGCTGC

TGGTGAAGCTGAACAGGGAAGATTTGCTCCGGAAGCAGAGGACCTTTGACAACGGTAGCATCCCCCACCAGATC

CACCTGGGCGAGCTGCACGCAATACTGAGGCGACAGGAGGATTTCTACCCCTTCCTCAAGGACAATAGGGAGAA

AATCGAAAAGATTCTGACCTTCAGGATCCCCTACTACGTGGGCCCTCTTGCCAGGGGCAACAGCCGATTCGCTT

GGATGACAAGAAAGAGCGAGGAGACCATCACCCCCTGGAACTTCGAGGAAGTGGTGGACAAAGGAGCAAGCGCG

CAGTCTTTCATCGAACGGATGACCAATTTCGACAAAAACCTGCCTAACGAGAAGGTGCTGCCCAAGCACAGCCT

GCTTTACGAGTACTTCACCGTGTACAACGAGCTCACCAAGGTGAAATATGTGACCGAGGGCATGCGAAAACCCG

CTTTCCTGAGCGGCGAGCAGAAGAAGGCCATCGTGGACCTGCTGTTCAAGACCAACAGGAAGGTGACCGTGAAG

CAGCTGAAGGAGGACTACTTCAAGAAGATCGAGTGCTTTGATAGCGTGGAAATAAGCGGCGTGGAGGACAGGTT

CAACGCCAGCCTGGGCACCTACCACGACTTGTTGAAGATAATCAAAGACAAGGATTTCCTGGATAATGAGGAGA

ACGAGGATATACTCGAGGACATCGTGCTGACTTTGACCCTGTTTGAGGACCGAGAGATGATTGAAGAAAGGCTC

AAAACCTACGCCCACCTGTTCGACGACAAAGTGATGAAACAACTGAAGAGACGAAGATACACCGGCTGGGGCAG

ACTGTCCAGGAAGCTCATCAACGGCATTAGGGACAAGCAGAGCGGCAAGACCATCCTGGATTTCCTGAAGTCCG

ACGGCTTCGCCAACCGAAACTTCATGCAGCTGATTCACGATGACAGCTTGACCTTCAAGGAGGACATCCAGAAG

GCCCAGGTTAGCGGCCAGGGCGACTCCCTGCACGAACATATTGCAAACCTGGCAGGCTCCCCTGCGATCAAGAA

GGGCATACTGCAGACCGTTAAGGTTGTGGACGAATTGGTCAAGGTCATGGGCAGGCACAAGCCCGAAAACATAG

TTATAGAGATGGCCAGAGAGAACCAGACCACCCAAAAGGGCCAGAAGAACAGCCGGGAGCGCATGAAAAGGATC

GAGGAGGGTATCAAGGAACTCGGAAGCCAGATCCTCAAAGAGCACCCCGTGGAGAATACCCAGCTCCAGAACGA

GAAGCTGTACCTGTACTACCTGCAGAACGGCAGGGACATGTACGTTGACCAGGAGTTGGACATCAACAGGCTTT

CAGACTATGACGTGGATCACATAGTGCCCCAGAGCTTTCTTAAAGACGATAGCATCGACAACAAGGTCCTGACC

CGCTCCGACAAAAACAGGGGCAAAAGCGACAACGTGCCAAGCGAAGAGGTGGTTAAAAAGATGAAGAACTACTG

GAGGCAACTGCTCAACGCGAAATTGATCACCCAGAGAAAGTTCGATAACCTGACCAAGGCCGAGAGGGGCGGAC

-continued

```
TCTCCGAACTTGACAAAGCGGGCTTCATAAAGAGGCAGCTGGTCGAGACCCGACAGATCACGAAGCACGTGGCC
CAAATCCTCGACAGCAGAATGAATACCAAGTACGATGAGAATGACAAACTCATCAGGGAAGTGAAAGTGATTAC
CCTGAAGAGCAAGTTGGTGTCCGACTTTCGCAAAGATTTCCAGTTCTACAAGGTGAGGGAGATCAACAACTACC
ACCATGCCCACGACGCATACCTGAACGCCGTGGTCGGCACCGCCCTGATTAAGAAGTATCCAAAGCTGGAGTCC
GAATTTGTCTACGGCGACTACAAAGTTTACGATGTGAGGAAGATGATCGCTAAGAGCGAACAGGAGATCGGCAA
GGCCACCGCTAAGTATTTCTTCTACAGCAACATCATGAACTTTTTCAAGACCGAGATCACACTTGCCAACGGCG
AAATCAGGAAGAGGCCGCTTATCGAGACCAACGGTGAGACCGGCGAGATCGTGTGGGACAAGGGCAGGGACTTC
GCCACCGTGAGGAAAGTCCTGAGCATGCCCCAGGTGAATATTGTGAAAAAAACTGAGGTGCAGACAGGCGGCTT
TAGCAAGGAATCCATCCTGCCCAAGAGGAACAGCGACAAGCTGATCGCCCGGAAGAAGGACTGGGACCCTAAGA
AGTATGGAGGCTTCGACAGCCCCACCGTAGCCTACAGCGTGCTGGTGGTCGCGAAGGTAGAGAAGGGGAAGAGC
AAGAAACTGAAGAGCGTGAAGGAGCTGCTCGGCATAACCATCATGGAGAGGTCCAGCTTTGAGAAGAACCCCAT
TGACTTTTTGGAAGCCAAGGGCTACAAAGAGGTCAAAAAGGACCTGATCATCAAACTCCCCAAGTACTCCCTGT
TTGAATTGGAGAACGGCAGAAAGAGGATGCTGGCGAGCGCTGGGGAACTGCAAAAGGGCAACGAACTGGCGCTG
CCCAGCAAGTACGTGAATTTTCTGTACCTGGCGTCCCACTACGAAAAGCTGAAAGGCAGCCCCGAGGACAACGA
GCAGAAGCAGCTGTTCGTGGAGCAGCACAAGCATTACCTGGACGAGATAATCGAGCAAATCAGCGAGTTCAGCA
AGAGGGTGATTCTGGCCGACGCGAACCTGGATAAGGTCCTCAGCGCCTACAACAAGCACCGAGACAAACCCATC
AGGGAGCAGGCCGAGAATATCATACACCTGTTCACCCTGACAAATCTGGGCGCACCTGCGGCATTCAAATACTT
CGATACCACCATCGACAGGAAAAGGTACACTAGCACTAAGGAGGTGCTGGATGCCACCTTGATCCACCAGTCCA
TTACCGGCCTGTATGAGACCAGGATCGACCTGAGCCAGCTTGGAGGCGACTCTAGGGCGGACCCAAAAAAGAAA
AGGAAGGTGGAATTCCACCACACTGGACTAGTGGATCCGAGCTCGGTACCAAGCTTAAGTTTAAACCGCTGA
```

R691A mutant SpyCas9 AA sequence.

SEQ ID NO: 4

```
MDKKYSIGLDIGTNSVGWAVITDEYKVPSKKFKVLGNTDRHSIKKNLIGALLFDSGETAEATRLKRTARRRYTR
RKNRICYLQEIFSNEMAKVDDSFFHRLEESFLVEEDKKHERHPIFGNIVDEVAYHEKYPTIYHLRKKLVDSTDK
ADLRLIYLALAHMIKFRGHFLIEGDLNPDNSDVDKLFIQLVQTYNQLFEENPINASGVDAKAILSARLSKSRRL
ENLIAQLPGEKKNGLFGNLIALSLGLTPNFKSNFDLAEDAKLQLSKDTYDDDLDNLLAQIGDQYADLFLAAKNL
SDAILLSDILRVNTEITKAPLSASMIKRYDEHHQDLTLLKALVRQQLPEKYKEIFFDQSKNGYAGYIDGGASQE
EFYKFIKPILEKMDGTEELLVKLNREDLLRKQRTFDNGSIPHQIHLGELHAILRRQEDFYPFLKDNREKIEKIL
TFRIPYYVGPLARGNSRFAWMTRKSEETITPWNFEEVVDKGASAQSFIERMTNFDKNLPNEKVLPKHSLLYEYF
TVYNELTKVKYVTEGMRKPAFLSGEQKKAIVDLLFKTNRKVTVKQLKEDYFKKIECFDSVEISGVEDRFNASLG
TYHDLLKIIKDKDFLDNEENEDILEDIVLTLTLFEDREMIEERLKTYAHLFDDKVMKQLKRRRYTGWGRLSRKL
INGIRDKQSGKTILDFLKSDGFANANFMQLIHDDSLTFKEDIQKAQVSGQGDSLHEHIANLAGSPAIKKGILQT
VKVVDELVKVMGRHKPENIVIEMARENQTTQKGQKNSRERMKRIEEGIKELGSQILKEHPVENTQLQNEKLYLY
YLQNGRDMYVDQELDINRLSDYDVDHIVPQSFLKDDSIDNKVLTRSDKNRGKSDNVPSEEVVKKMKNYWRQLLN
AKLITQRKFDNLTKAERGGLSELDKAGFIKRQLVETRQITKHVAQILDSRMNTKYDENDKLIREVKVITLKSKL
VSDFRKDFQFYKVREINNYHHAHDAYLNAVVGTALIKKYPKLESEFVYGDYKVYDVRKMIAKSEQEIGKATAKY
FFYSNIMNFFKTEITLANGEIRKRPLIETNGETGEIVWDKGRDFATVRKVLSMPQVNIVKKTEVQTGGFSKESI
LPKRNSDKLIARKKDWDPKKYGGFDSPTVAYSVLVVAKVEKGKSKKLKSVKELLGITIMERSSFEKNPIDFLEA
KGYKEVKKDLIIKLPKYSLFELENGRKRMLASAGELQKGNELALPSKYVNFLYLASHYEKLKGSPEDNEQKQLF
VEQHKHYLDEIIEQISEFSKRVILADANLDKVLSAYNKHRDKPIREQAENIIHLFTLTNLGAPAAFKYFDTTID
RKRYTSTKEVLDATLIHQSITGLYETRIDLSQLGGD
```

-continued

R691A mutant SpyCas9 DNA sequence, codon optimized for expression in *E. coli*.
SEQ ID NO: 5

ATGGGCAGCAGCGCCCCAAAGAAGAAGCGGAAGGTCGGTATCCACGGAGTCCCAGCAGCCATGGACAAAAAGTA

CTCTATTGGCCTGGATATCGGGACCAACAGCGTCGGGTGGGCTGTTATCACCGACGAGTATAAAGTACCTTCGA

AAAAGTTCAAAGTGCTGGGCAACACCGATCGCCATTCAATCAAAAAGAACTTGATTGGTGCGCTGTTGTTTGAC

TCCGGGGAAACCGCCGAGGCGACTCGCCTTAAACGTACAGCACGTCGCCGGTACACTCGGCGTAAGAATCGCAT

TTGCTATTTGCAGGAAATCTTTAGCAACGAGATGGCAAAAGTCGATGACTCGTTTTTCCACCGCCTCGAGGAAA

GCTTTCTGGTGGAGGAAGACAAAAAGCATGAGCGTCACCCGATCTTCGGCAACATTGTCGATGAAGTAGCGTAT

CATGAAAAATACCCAACCATTTACCACTTACGCAAAAAGCTGGTGGACAGCACTGACAAAGCTGATTTGCGCCT

TATCTATTTAGCCCTGGCACATATGATTAAGTTTCGTGGTCACTTCCTGATCGAAGGAGACTTAAATCCCGACA

ACAGTGATGTTGATAAATTGTTTATTCAGCTTGTCCAAACTTACAATCAACTGTTCGAGGAAAACCCGATCAAT

GCCTCCGGTGTGGATGCAAAAGCCATTTTAAGTGCACGCCTTAGCAAGTCCCGTCGCTTAGAAAACCTTATCGC

GCAGCTGCCCGGCGAGAAAAAGAATGGTTTGTTTGGGAACCTTATTGCCTTGAGCTTAGGCCTCACCCCGAATT

TCAAAAGTAATTTCGATCTTGCAGAAGACGCCAAATTACAACTGTCGAAGGATACTTATGATGACGATCTCGAT

AATCTGTTAGCGCAGATTGGTGACCAATACGCCGATCTTTTTCTGGCGGCTAAAAATCTGAGCGACGCCATCTT

GCTTTCGGATATTCTCCGCGTTAACACCGAAATCACGAAAGCGCCTCTTAGTGCCAGCATGATTAAACGTTATG

ATGAACACCACCAGGACCTGACCTTACTCAAAGCGTTGGTTCGCCAGCAACTGCCAGAGAAGTACAAAGAAATC

TTCTTTGATCAGTCAAAGAATGGTTATGCCGGCTATATTGACGGGGGTGCAAGCAAGAGGAATTCTACAAATT

TATCAAGCCTATTCTGGAGAAAATGGATGGCACCGAAGAGTTATTGGTGAAGCTTAACCGTGAAGACCTCCTGC

GGAAACAGCGCACATTCGATAATGGTTCGATCCCACACCCAAATCCATTTGGGGGAGTTACACGCTATTTTGCGT

CGCCAGGAAGACTTTTACCCTTTCCTGAAGGATAACCGGGAGAAAATTGAGAAGATCCTTACCTTTCGTATTCC

GTATTACGTAGGCCCCTTAGCACGGGGTAATAGCCGTTTCGCGTGGATGACACGGAAGTCGGAAGAGACGATCA

CCCCGTGGAACTTCGAAGAGGTAGTCGACAAGGGCGCATCAGCGCAGTCTTTTATTGAACGTATGACGAATTTC

GATAAAAACTTGCCCAATGAGAAGGTGCTTCCGAAACATTCCTTGTTATATGAATATTTTACAGTTTACAACGA

GCTGACCAAGGTTAAATACGTGACGGAAGGAATGCGCAAGCCCGCTTTTCTTAGCGGTGAGCAAAAAAAGGCGA

TCGTCGACCTGTTATTCAAAACGAATCGTAAGGTGACTGTAAAGCAACTCAAAGAAGATTACTTCAAAAAGATT

GAGTGCTTCGACAGCGTCGAAATCTCTGGGGTAGAGGATCGGTTTAACGCAAGTTTAGGTACCTACCATGACCT

GCTTAAAATCATTAAGGATAAAGACTTCTTAGATAATGAAGAGAACGAAGATATTCTCGAGGACATCGTCTTGA

CGTTAACCTTATTTGAGGATCGTGAAATGATTGAGGAACGCCTCAAAACTTATGCCCACCTGTTCGACGATAAG

GTGATGAAGCAGCTGAAACGTCGGCGCTACACAGGATGGGGCCGCTTGAGTCGCAAACTTATTAACGGAATCCG

TGACAAGCAATCCGGCAAAACGATTCTGGATTTCTTGAAGTCGGACGGATTTGCTAATGCGAACTTCATGCAGT

TGATCCATGATGACTCCCTGACTTTTAAAGAGGATATTCAAAAGGCGCAGGTTAGTGGTCAAGGCGACAGCTTA

CACGAACACATCGCAAATTTGGCTGGTTCGCCGGCCATTAAAAAGGGGATCCTCCAGACCGTGAAAGTTGTAGA

TGAGCTTGTTAAGGTCATGGGTCGTCATAAGCCCGAAAACATCGTGATTGAAATGGCGCGGGAGAATCAAACGA

CCCAGAAAGGACAAAAGAATAGCCGTGAACGGATGAAGCGGATCGAGGAAGGCATTAAAGAGCTGGGGTCTCAA

ATCTTGAAGGAACACCCTGTGGAGAACACTCAGCTCCAAAATGAAAAACTTTACCTGTACTATTTGCAGAACGG

ACGCGATATGTACGTGGACCAAGAGTTGGATATTAATCGGCTGAGTGACTACGACGTTGATCATATCGTCCCGC

AGAGCTTCCTCAAAGACGATTCTATTGACAATAAGGTACTGACGCGCTCTGATAAAAACCGTGGTAAGTCGGAC

AACGTGCCCTCCGAAGAGGTTGTGAAAAAGATGAAAAATTATTGGCGCCAGCTTTTAAACGCGAAGCTGATCAC

ACAACGTAAATTCGATAATTTGACCAAGGCTGAACGGGGTGGCCTGAGCGAGTTAGATAAGGCAGGATTTATTA

AACGCCAGTTAGTGGAGACTCGTCAAATCACCCAAACATGTCGCGCAGATTTTGGACAGCCGGATGAACACCAAG

TAGGATGAAAATGACAAACTGATCCGTGAGGTGAAAGTCATTACTCTGAAGTCCAAATTAGTTAGTGATTTCCG

-continued

```
GAAGGACTTTCAATTCTACAAAGTCCGTGAAATTAATAACTATCATCACGCACATGACGCGTACCTGAATGCAG
TGGTTGGGACCGCCCTTATCAAGAAATATCCTAAGCTGGAGTCGGAGTTTGTCTATGGCGACTATAAGGTATAC
GATGTTCGCAAAATGATTGCGAAATCTGAGCAGGAGATCGGTAAGGCAACCGCAAAATATTTCTTTTACTCAAA
CATTATGAATTTCTTTAAGACAGAAATCACTCTGGCCAACGGGGAGATTCGCAAACGTCCGTTGATCGAAACAA
ACGGCGAGACTGGCGAAATTGTTTGGGACAAAGGGCGTGATTTCGCGACGGTGCGCAAGGTACTGAGCATGCCT
CAAGTCAATATTGTTAAGAAAACCGAAGTGCAGACGGGCGGGTTTTCCAAGGAAAGCATCTTACCCAAACGTAA
TTCAGATAAACTTATTGCACGCAAAAAGGACTGGGATCCGAAAAAGTATGGAGGCTTCGACAGTCCAACCGTAG
CCTACTCTGTTCTCGTTGTAGCGAAAGTAGAAAAGGGTAAATCCAAGAAACTGAAATCTGTCAAGGAGTTGCTT
GGAATCACCATTATGGAGCGTAGCTCCTTCGAGAAGAACCCGATTGACTTTCTGGAAGCCAAAGGATATAAAGA
GGTCAAGAAAGATCTTATCATTAAGCTGCCTAAGTATTCACTCTTCGAGCTGGAAAATGGTCGTAAACGCATGC
TCGCTTCTGCCGGCGAGTTGCAGAAGGGCAATGAATTAGCACTTCCATCAAAGTACGTTAACTTCCTGTATTTG
GCCAGCCATTACGAGAAACTGAAGGGGTCTCCAGAGGACAACGAACAGAAACAATTATTTGTAGAGCAGCACAA
GCATTATCTTGATGAAATCATTGAGCAAATTTCCGAATTCAGTAAACGCGTAATCCTGGCCGATGCAAACCTCG
ACAAGGTGCTGAGCGCTTACAATAAGCATCGCGACAAACCTATCCGTGAGCAGGCTGAAAATATCATTCACCTG
TTCACATTAACGAACCTGGGCGCTCCGGCCGCTTTTAAATATTTCGACACGACAATCGACCGTAAGCGCTATAC
CAGTACGAAAGAAGTGTTGGATGCGACCCTTATTCACCAGTCAATTACAGGATTATATGAGACCCGTATCGACC
TTAGCCAATTAGGTGGGGATGCGGCCCCGAAGAAAAAACGCAAAGTGGATCCGAAGAAAAAACGCAAAGTGGCG
GCCGCACTCGAGCACCACCACCACCACCACTGA
```

R691A mutant SpyCas9 DNA sequence, codon optimized for expression in H. sapiens.

SEQ ID NO: 6

```
ATGGGCAAGCCCATCCCTAACCCCCTGTTGGGGCTGGACAGCACCGCTCCCAAAAAGAAAAGGAAGGTGGGCAT
TCACGGCGTGCCTGCGGCCGACAAAAAGTACAGCATCGGCCTTGATATCGGCACCAATAGCGTGGGCTGGGCCG
TTATCACAGACGAATACAAGGTACCCAGCAAGAAGTTCAAGGTGCTGGGGAATACAGACAGGCACTCTATCAAG
AAAAACCTTATCGGGGCTCTGCTGTTTGACTCAGGCGAGACCGCCGAGGCCACCAGGTTGAAGAGGACCGCAAG
GCGAAGGTACACCCGGAGGAAGAACAGGATCTGCTATCTGCAGGAGATCTTCAGCAACGAGATGGCCAAGGTGG
ACGACAGCTTCTTCCACAGGCTGGAGGAGAGCTTCCTTGTCGAGGAGGATAAGAAGCACGAACGACACCCCATC
TTCGGCAACATAGTCGACGAGGTCGCTTATCACGAGAAGTACCCCACCATCTACCACCTGCGAAAGAAATTGGT
GGATAGCACCGATAAAGCCGACTTGCGACTTATCTACTTGGCTCTGGCGCACATGATTAAGTTCAGGGGCCACT
TCCTGATCGAGGGCGACCTTAACCCCGACAACAGTGACGTAGACAAATTGTTCATCCAGCTTGTACAGACCTAT
AACCAGCTGTTCGAGGAAAACCCTATTAACGCCAGCGGGTGGATGCGAAGGCCATACTTAGCGCCAGGCTGAG
CAAAAGCAGGCGCTTGGAGAACCTGATAGCCCAGCTGCCCGGTGAAAAGAAGAACGGCCTCTTCGGTAATCTGA
TTGCCCTGAGCCTGGGCCTGACCCCCAACTTCAAGAGCAACTTCGACCTGGCAGAAGATGCCAAGCTGCAGTTG
AGTAAGGACACCTATGACGACGACTTGGACAATCTGCTCGCCCAAATCGGCGACCAGTACGCTGACCTGTTCCT
CGCCGCCAAGAACCTTTCTGACGCAATCCTGCTTAGCGATATCCTTAGGGTGAACACAGAGATCACCAAGGCCC
CCCTGAGCGCCAGCATGATCAAGAGGTACGACGAGCACCATCAGGACCTGACCCTTCTGAAGGCCCTGGTGAGG
CAGCAACTGCCCGAGAAGTACAAGGAGATCTTTTTCGACCAGAGCAAGAACGGCTACGCCGGCTACATCGACGG
CGGAGCCAGCCAAGAGGAGTTCTACAAGTTCATCAAGCCCATCCTGGAGAAGATGGATGGCACCGAGGAGCTGC
TGGTGAAGCTGAACAGGGAAGATTTGCTCCGGAAGCAGAGGACCTTTGACAACGGTAGCATCCCCCACCAGATC
CACCTGGGCGAGCTGCACGCAATACTGAGGCGACAGGAGGATTTCTACCCCTTCCTCAAGGACAATAGGGAGAA
AATCGAAAAGATTCTGACCTTCAGGATCCCCTACTACGTGGGCCCTCTTGCCAGGGGCAACAGCCGATTCGCTT
GGATGACAAGAAAGAGCGAGGAGACCATCACCCCCTGGAACTTCGAGGAAGTGGTGGACAAAGGAGCAAGCGCG
```

-continued

```
CAGTCTTTCATCGAACGGATGACCAATTTCGACAAAAACCTGCCTAACGAGAAGGTGCTGCCCAAGCACAGCCT

GCTTTACGAGTACTTCACCGTGTACAACGAGCTCACCAAGGTGAAATATGTGACCGAGGGCATGCGAAAACCCG

CTTTCCTGAGCGGCGAGCAGAAGAAGGCCATCGTGGACCTGCTGTTCAAGACCAACAGGAAGGTGACCGTGAAG

CAGCTGAAGGAGGACTACTTCAAGAAGATCGAGTGCTTTGATAGCGTGGAAATAAGCGGCGTGGAGGACAGGTT

CAACGCCAGCCTGGGCACCTACCACGACTTGTTGAAGATAATCAAAGACAAGGATTTCCTGGATAATGAGGAGA

ACGAGGATATACTCGAGGACATCGTGCTGACTTTGACCCTGTTTGAGGACCGAGAGATGATTGAAGAAAGGCTC

AAAACCTACGCCCACCTGTTCGACGACAAAGTGATGAAACAACTGAAGAGACGAAGATACACCGGCTGGGGCAG

ACTGTCCAGGAAGCTCATCAACGGCATTAGGGACAAGCAGAGCGGCAAGACCATCCTGGATTTCCTGAAGTCCG

ACGGCTTCGCCAACGCCAACTTCATGCAGCTGATTCACGATGACAGCTTGACCTTCAAGGAGGACATCCAGAAG

GCCCAGGTTAGCGGCCAGGGCGACTCCCTGCACGAACATATTGCAAACCTGGCAGGCTCCCCTGCGATCAAGAA

GGGCATACTGCAGACCGTTAAGGTTGTGGACGAATTGGTCAAGGTCATGGGCAGGCACAAGCCCGAAAACATAG

TTATAGAGATGGCCAGAGAGAACCAGACCACCCAAAAGGGCCAGAAGAACAGCCGGGAGCGCATGAAAAGGATC

GAGGAGGGTATCAAGGAACTCGGAAGCCAGATCCTCAAAGAGCACCCCGTGGAGAATACCCAGCTCCAGAACGA

GAAGCTGTACCTGTACTACCTGCAGAACGGCAGGGACATGTACGTTGACCAGGAGTTGGACATCAACAGGCTTT

CAGACTATGACGTGGATCACATAGTGCCCCAGAGCTTTCTTAAAGACGATAGCATCGACAACAAGGTCCTGACC

CGCTCCGACAAAAACAGGGGCAAAAGCGACAACGTGCCAAGCGAAGAGGTGGTTAAAAAGATGAAGAACTACTG

GAGGCAACTGCTCAACGCGAAATTGATCACCCAGAGAAAGTTCGATAACCTGACCAAGGCCGAGAGGGGCGGAC

TCTCCGAACTTGACAAAGCGGGCTTCATAAAGAGGCAGCTGGTCGAGACCCGACAGATCACGAAGCACGTGGCC

CAAATCCTCGACAGCAGAATGAATACCAAGTACGATGAGAATGACAAACTCATCAGGGAAGTGAAAGTGATTAC

CCTGAAGAGCAAGTTGGTGTCCGACTTTCGCAAAGATTTCCAGTTCTACAAGGTGAGGGAGATCAACAACTACC

ACCATGCCCACGACGCATACCTGAACGCCGTGGTCGGCACCGCCCTGATTAAGAAGTATCCAAAGCTGGAGTCC

GAATTTGTCTACGGCGACTACAAAGTTTACGATGTGAGGAAGATGATCGCTAAGAGCGAACAGGAGATCGGCAA

GGCCACCGCTAAGTATTTCTTCTACAGCAACATCATGAACTTTTTCAAGACCGAGATCACACTTGCCAACGGCG

AAATCAGGAAGAGGCCGCTTATCGAGACCAACGGTGAGACCGGCGAGATCGTGTGGGACAAGGGCAGGGACTTC

GCCACCGTGAGGAAAGTCCTGAGCATGCCCCAGGTGAATATTGTGAAAAAAACTGAGGTGCAGACAGGCGGCTT

TAGCAAGGAATCCATCCTGCCCAAGAGGAACAGCGACAAGCTGATCGCCCGGAAGAAGGACTGGGACCCTAAGA

AGTATGGAGGCTTCGACAGCCCCACCGTAGCCTACAGCGTGCTGGTGGTCGCGAAGGTAGAGAAGGGGAAGAGC

AAGAAACTGAAGAGCGTGAAGGAGCTGCTCGGCATAACCATCATGGAGAGGTCCAGCTTTGAGAAGAACCCCAT

TGACTTTTTGGAAGCCAAGGGCTACAAAGAGGTCAAAAAGGACCTGATCATCAAACTCCCCAAGTACTCCCTGT

TTGAATTGGAGAACGGCAGAAAGAGGATGCTGGCGAGCGCTGGGGAACTGCAAAAGGGCAACGAACTGGCGCTG

CCCAGCAAGTACGTGAATTTTCTGTACCTGGCGTCCCACTACGAAAAGCTGAAAGGCAGCCCCGAGGACAACGA

GCAGAAGCAGCTGTTCGTGGAGCAGCACAAGCATTACCTGGACGAGATAATCGAGCAAATCAGCGAGTTCAGCA

AGAGGGTGATTCTGGCCGACGCGAACCTGGATAAGGTCCTCAGCGCCTACAACAAGCACCGAGACAAACCCATC

AGGGAGCAGGCCGAGAATATCATACACCTGTTCACCCTGACAAATCTGGGCGCACCTGCGGCATTCAAATACTT

CGATACCACCATCGACAGGAAAAGGTACACTAGCACTAAGGAGGTGCTGGATGCCACCTTGATCCACCAGTCCA

TTACCGGCCTGTATGAGACCAGGATCGACCTGAGCCAGCTTGGAGGCGACTCTAGGGCGGACCCAAAAAAGAAA

AGGAAGGTGGAATTCCACCACACTGGACTAGTGGATCCGAGCTCGGTACCAAGCTTAAGTTTAAACCGCTGA
```

REFERENCES

[1] Vakulskas C A, et al. A high-fidelity Cas9 mutant delivered as a ribonucleoprotein complex enables efficient gene editing in human hematopoietic stem and progenitor cells. *Nat Med.* 2018 August; 24(8):1216-1224.

[2] Walton R T, Christie K A, Whittaker M N, Kleinstiver B P. Unconstrained genome targeting with near-PAMless engineered CRISPR-Cas9 variants. *Science.* 2020; 368 (6488):290-296.

[3] Kim H K, Yu G, Park J, et al. Predicting the efficiency of prime editing guide RNAs in human cells. *Nat Biotechnol.* 2021; 39(2):198-206.

[4] Song M, Kim H K, Lee S, et al. Sequence-specific prediction of the efficiencies of adenine and cytosine base editors. *Nat Biotechnol.* 2020; 38(9):1037-1043.

[5] Anzalone A V, Randolph P B, Davis J R, et al. Search-and-replace genome editing without double-strand breaks or donor DNA. *Nature.* 2019; 576(7785):149-157.

All references, including publications, patent applications, and patents, cited herein are hereby incorporated by reference to the same extent as if each reference were individually and specifically indicated to be incorporated by reference and were set forth in its entirety herein.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. An isolated mutant Cas9 protein, wherein the isolated mutant Cas9 protein is active in a CRISPR/Cas endonuclease system, wherein the CRISPR/Cas endonuclease system displays increased on-target editing activity relative to a wild-type CRISPR/Cas endonuclease system having a wild-type Cas9 protein of SEQ ID NO:1, wherein the isolated mutant Cas9 protein comprises the double amino acid substitution D54A/R691A introduced into SEQ ID NO:1.

2. An isolated ribonucleoprotein complex, comprising:
a mutant Cas9 protein; and
a gRNA complex,
wherein the isolated ribonucleoprotein complex is active as a CRISPR/Cas endonuclease system, wherein the resultant CRISPR/Cas endonuclease system displays increased on-target editing activity relative to a wild-type CRISPR/Cas endonuclease system having a wild-type Cas9 protein of SEQ ID NO:1, wherein the mutant Cas9 protein comprises the double amino acid substitution D54A/R691A introduced into SEQ ID NO:1.

3. The isolated ribonucleoprotein complex of claim 2, wherein the gRNA comprises a crRNA and a tracrRNA in stoichiometric ratio.

4. The isolated ribonucleoprotein complex of claim 3, wherein the gRNA comprises:
an isolated crRNA comprises an isolated, synthetic crRNA directed against a specific editing target site for a given locus; and
the tracrRNA comprises an isolated, synthetic tracrRNA.

5. The isolated ribonucleoprotein complex of claim 3, wherein the gRNA comprises a sgRNA.

6. An isolated nucleic acid encoding a mutant Cas9 protein, wherein the mutant Cas9 protein is active in a CRISPR/Cas endonuclease system, wherein the CRISPR/Cas endonuclease system displays increased on-target editing activity relative to a wild-type CRISPR/Cas endonuclease system having a wild-type Cas9 protein of SEQ ID NO: 1, wherein the mutant Cas9 protein comprises the double amino acid substitution D54A/R691A introduced into SEQ ID NO:1.

7. A CRISPR/Cas endonuclease system comprising a mutant Cas9 protein and a gRNA, wherein the CRISPR/Cas endonuclease system displays increased on-target editing activity relative to a wild-type CRISPR/Cas endonuclease system having a wild-type Cas9 protein of SEQ ID NO:1, wherein the mutant Cas9 protein comprises the double amino acid substitution D54A/R691A introduced into SEQ ID NO:1.

8. The CRISPR/Cas endonuclease system of claim 7, wherein the CRISPR/Cas endonuclease system further comprises a DNA expression vector, wherein the mutant Cas9 protein is encoded by the DNA expression vector.

9. The CRISPR/Cas endonuclease system of claim 8, wherein the DNA expression vector comprises a plasmid-borne vector.

10. The CRISPR/Cas endonuclease system of claim 8, wherein the DNA expression vector is selected from a bacterial expression vector and a eukaryotic expression vector.

11. The CRISPR/Cas endonuclease system of claim 7, wherein the gRNA includes a crRNA and a tracrRNA in stoichiometric ratio.

12. The CRISPR/Cas endonuclease system of claim 11, wherein the crRNA comprises an isolated, synthetic crRNA directed against a specific editing target site for a given locus and the tracrRNA comprises an isolated, synthetic tracrRNA.

13. The CRISPR/Cas endonuclease system of claim 7, wherein the gRNA comprises a sgRNA.

14. A method of performing gene editing having increased on-target editing activity, comprising:
contacting a candidate editing target site locus with an active CRISPR/Cas endonuclease system having a mutant Cas9 protein, wherein the active CRISPR/Cas endonuclease system displays increased on-target editing activity relative to a wild-type CRISPR/Cas endonuclease system having a wild-type Cas9 protein of SEQ ID NO:1, wherein the mutant Cas9 protein comprises the double amino acid substitution D54A/R691A introduced into SEQ ID NO:1.

* * * * *